US010913745B2

(12) United States Patent
Hert et al.

(10) Patent No.: US 10,913,745 B2
(45) Date of Patent: Feb. 9, 2021

(54) OCTAHYDRO-PYRROLO[3,4-C]-PYRROLE DERIVATIVES AND ANALOGS THEREOF AS AUTOTAXIN INHIBITORS

(71) Applicant: Hoffmann-La Roche Inc., Little Falls, NJ (US)

(72) Inventors: Jerome Hert, Basel (CH); Daniel Hunziker, Moehlin (CH); Patrizio Mattei, Riehen (CH); Harald Mauser, Riehen (CH); Guozhi Tang, Shanghai (CN); Lisha Wang, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/975,528

(22) Filed: May 9, 2018

(65) Prior Publication Data

US 2018/0258095 A1    Sep. 13, 2018

Related U.S. Application Data

(63) Continuation of application No. 14/850,497, filed on Sep. 10, 2015, now abandoned, which is a continuation of application No. PCT/EP2014/054631, filed on Mar. 11, 2014.

(30) Foreign Application Priority Data

Mar. 12, 2013 (EP) .................... 13158724

(51) Int. Cl.
*C07D 487/04* (2006.01)
*C07D 471/04* (2006.01)

(52) U.S. Cl.
CPC ........ *C07D 487/04* (2013.01); *C07D 471/04* (2013.01)

(58) Field of Classification Search
CPC ............................ C07D 487/04; C07D 471/04
See application file for complete search history.

(56) References Cited

U.S. PATENT DOCUMENTS

| | | | |
|---|---|---|---|
| 3,392,149 A | 7/1968 | von der Emden et al. |
| 5,202,322 A | 4/1993 | Allen et al. |
| 5,238,942 A | 8/1993 | Chakravarty et al. |
| 5,240,928 A | 8/1993 | Allen et al. |
| 5,290,780 A | 3/1994 | Venkatesan et al. |
| 5,304,565 A | 4/1994 | Morimoto et al. |
| 5,358,951 A | 10/1994 | Levin et al. |
| 5,470,975 A | 11/1995 | Meier et al. |
| 5,472,961 A | 12/1995 | Gottschlich et al. |
| 5,532,243 A | 7/1996 | Gilligan |
| 6,821,964 B2 | 11/2004 | Colon-Cruz et al. |
| 6,841,560 B2 | 1/2005 | Thompson et al. |
| 7,271,260 B2 | 9/2007 | Lee et al. |
| 8,329,907 B2 | 11/2012 | Schultz et al. |
| 8,440,694 B2 | 5/2013 | Turner et al. |
| 8,697,883 B2 | 4/2014 | Abouabdellah et al. |
| 8,841,324 B2 | 9/2014 | Staehle et al. |
| 8,946,264 B2 | 2/2015 | Shinozuka et al. |
| 9,029,387 B2 | 5/2015 | Staehle et al. |
| 9,493,486 B2 | 11/2016 | Hunziker et al. |
| 9,580,434 B2 | 2/2017 | Mazurov et al. |
| 9,598,418 B2 | 3/2017 | Srivastava et al. |
| 9,802,944 B2 | 10/2017 | Di Giorgio et al. |
| 10,208,052 B1 | 2/2019 | Zheng et al. |
| 10,633,384 B2 | 4/2020 | Hunziker et al. |
| 10,640,472 B2 | 5/2020 | Hert et al. |
| 10,647,719 B2 | 5/2020 | Di Giorgio et al. |
| 10,654,857 B2 | 5/2020 | Di Giorgio et al. |
| 10,669,268 B2 | 6/2020 | Hert et al. |
| 10,669,285 B2 | 6/2020 | Hunziker et al. |
| 10,676,446 B2 | 6/2020 | Hert et al. |
| 2005/0203112 A1 | 9/2005 | Castonguay et al. |
| 2008/0090802 A1 | 4/2008 | Letourneau et al. |
| 2010/0222341 A1 | 9/2010 | Schiemann et al. |
| 2010/0298290 A1 | 11/2010 | Anand et al. |
| 2011/0230471 A1 | 9/2011 | Staehle et al. |
| 2012/0015959 A1 | 1/2012 | Staehle et al. |
| 2012/0095040 A1 | 4/2012 | Abouabdellah et al. |
| 2012/0115852 A1 | 5/2012 | Schultz et al. |
| 2012/0115858 A1 | 5/2012 | Tesconi et al. |

(Continued)

FOREIGN PATENT DOCUMENTS

CA   2768095      1/2011
CA   2878442 A1   4/2014

(Continued)

OTHER PUBLICATIONS

Lupus [online], retrieved from the internet on Jan. 24, 2017; http://www.mayoclinic.org/diseases-conditions/lupus/basics/definition/CON-20019676.*

(Continued)

*Primary Examiner* — Shawquia Jackson

(74) *Attorney, Agent, or Firm* — Katherine J. Mackenzie

(57) ABSTRACT

The invention provides novel compounds having the general formula (I)

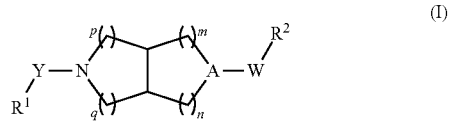

wherein $R^1$, Y, A, W, $R^2$, m, n, p and q are as described herein, compositions including the compounds and methods of using the compounds.

39 Claims, No Drawings

(56) References Cited

U.S. PATENT DOCUMENTS

| | | |
|---|---|---|
| 2015/0252046 A1 | 9/2015 | Staehle et al. |
| 2015/0353559 A1 | 12/2015 | Hert et al. |
| 2015/0376194 A1 | 12/2015 | Hert et al. |
| 2016/0264586 A1 | 9/2016 | Mattei et al. |
| 2017/0008900 A1 | 1/2017 | Di Giorgio et al. |
| 2017/0008913 A1 | 1/2017 | Hunziker et al. |
| 2017/0029425 A1 | 2/2017 | Hunziker et al. |
| 2017/0050960 A1 | 2/2017 | Hert et al. |
| 2018/0208601 A1 | 7/2018 | Hert et al. |
| 2018/0208602 A1 | 7/2018 | Di Giorgio et al. |
| 2018/0258095 A1 | 9/2018 | Hert et al. |
| 2018/0280352 A1 | 10/2018 | Mattei et al. |
| 2018/0312515 A1 | 11/2018 | Mattei et al. |
| 2018/0327410 A1 | 11/2018 | Grice et al. |
| 2018/0327416 A1 | 11/2018 | Grice et al. |
| 2020/0002297 A1 | 1/2020 | Mattei et al. |
| 2020/0002336 A1 | 1/2020 | Hert et al. |
| 2020/0079779 A1 | 3/2020 | Di Giorgio et al. |
| 2020/0087307 A1 | 3/2020 | Mattei et al. |
| 2020/0199155 A1 | 6/2020 | Hunziker et al. |
| 2020/0207769 A1 | 7/2020 | Hunziker et al. |
| 2020/0216457 A1 | 7/2020 | Di Giorgio et al. |

FOREIGN PATENT DOCUMENTS

| | | |
|---|---|---|
| CN | 1068114 A | 1/1993 |
| CN | 1751047 A1 | 3/2006 |
| CN | 102459207 A | 5/2012 |
| CN | 103237799 A | 8/2013 |
| CN | 104428299 A | 3/2015 |
| CN | 104918917 A | 9/2015 |
| EP | 0 417 631 A2 | 3/1991 |
| EP | 0 424 850 A1 | 5/1991 |
| EP | 2 301 936 A1 | 3/2011 |
| EP | 3 187 492 A1 | 7/2017 |
| EP | 3385261 A1 | 10/2018 |
| JP | 2001039950 | 2/2001 |
| JP | 2005-239708 | 9/2005 |
| JP | 2007-176809 | 7/2007 |
| JP | 2008-501743 | 1/2008 |
| JP | 2008-31064 | 2/2008 |
| JP | 2008-31064 A | 2/2008 |
| JP | 2008-531533 | 8/2008 |
| JP | 2008-540547 | 11/2008 |
| JP | 2009-161449 | 7/2009 |
| JP | 2011-502150 | 1/2011 |
| KR | 2006-0088557 | 8/2006 |
| RU | 2375352 C2 | 12/2009 |
| RU | 2 480 463 | 4/2013 |
| RU | 2 483 068 | 5/2013 |
| RU | 2 517 693 | 5/2014 |
| WO | 99/40070 | 8/1999 |
| WO | 01/30780 | 5/2001 |
| WO | 02/070523 A1 | 9/2002 |
| WO | 2004/074291 A1 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/090143 | 8/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | 2008/135141 A1 | 11/2008 |
| WO | 2009/046841 A2 | 4/2009 |
| WO | 2009/054914 A1 | 4/2009 |
| WO | 2009/058347 | 5/2009 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108268 | 9/2010 |
| WO | 2010/108651 | 9/2010 |
| WO | 2010/112116 A1 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/141817 A1 | 12/2010 |
| WO | 2011/006569 A1 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 A1 | 9/2011 |
| WO | 2011/141716 A2 | 11/2011 |
| WO | 2009/154132 | 12/2011 |
| WO | 2011/151461 A2 | 12/2011 |
| WO | 2012/020008 | 2/2012 |
| WO | 2012/024620 | 2/2012 |
| WO | 2012/028243 | 3/2012 |
| WO | 2012/080727 | 6/2012 |
| WO | 2012/166415 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2013/186159 | 12/2013 |
| WO | 2014/007951 | 1/2014 |
| WO | 2014/018881 | 1/2014 |
| WO | 2014/018891 A1 | 1/2014 |
| WO | 2014/048865 A1 | 4/2014 |
| WO | 2014/048881 | 4/2014 |
| WO | 2014/055548 | 4/2014 |
| WO | 2014/066659 | 5/2014 |
| WO | 2014/102817 A1 | 7/2014 |
| WO | 2014/133112 A1 | 9/2014 |
| WO | 2014/139324 | 9/2014 |
| WO | 2014/139978 A1 | 9/2014 |
| WO | 2014/143579 | 9/2014 |
| WO | 2014/152725 A1 | 9/2014 |
| WO | 2014/164905 | 10/2014 |
| WO | 2015/008230 A1 | 1/2015 |
| WO | 2015/058031 | 4/2015 |
| WO | 2015/077503 A1 | 5/2015 |
| WO | 2015/078800 A1 | 6/2015 |
| WO | 2015/078803 | 6/2015 |
| WO | 2015/144480 A1 | 10/2015 |
| WO | 2015/144605 A1 | 10/2015 |
| WO | 2015/144609 A1 | 10/2015 |
| WO | 2015/144803 A1 | 10/2015 |
| WO | 2015/154023 A1 | 10/2015 |
| WO | 2016/031987 | 3/2016 |
| WO | 2016/061160 A1 | 4/2016 |
| WO | 2016/128529 A1 | 8/2016 |
| WO | 2016/162390 | 10/2016 |
| WO | 2017/005073 | 1/2017 |
| WO | 2017/037146 | 3/2017 |
| WO | 2017/037670 A1 | 3/2017 |
| WO | 2017/050732 | 3/2017 |
| WO | 2017/050747 | 3/2017 |
| WO | 2017/050791 | 3/2017 |
| WO | 2017/050792 | 3/2017 |
| WO | 2017/053722 A1 | 3/2017 |
| WO | 2017/091673 A2 | 6/2017 |

(56) References Cited

FOREIGN PATENT DOCUMENTS

| WO | 2017/139978 | 8/2017 |
|---|---|---|
| WO | 2018/167001 A1 | 9/2018 |
| WO | 2018/167113 A1 | 9/2018 |

OTHER PUBLICATIONS 1206969-43-8,Database Registry [retrieved online May 25, 2016] Chemical Abstracts Service, Feb. 22, 2010 (Feb. 22, 2010), BroadPharm: XP002707619, retrieved from STN Database accession No. 1206969-43-8 the whole document.
959567-58-9,Database Registry [retrieved online May 25, 2016] Chemical Abstracts Service Dec. 26, 2007 (Dec. 26, 2007), NIH Chemical Genomics Center: XP002707620, retrieved from STN Database accession No. 959567-58-9.
Albers et al., "Chemical Evolution of Autotaxin Inhibitors" Chemical Reviews (XP055073234), 112(5):2593-2603 (May 9, 2012).
Barbayianni et al., "Autotaxin inhibitors: a patient review" Expert Opin Ther Patents 23(9):1123-1132 ( 2013).
Benesh et al., FEBS LETT 588:2712-2727 ( 2014).
CAS Registry Database, 1300725-30-7,Database Registry [retrieved online May 25, 2016] Chemical Abstracts Service May 25, 2011 (May 25, 2011), Focus Synthesis LLC: XP002707618, retrieved from STN Database accession No. 1300725-30-7 the whole document.
CAS Registry Database, 1352926-14-7,Database Registry [retrieved online May 25, 2016] Chemical Abstracts Service Jan. 12, 2012 (Jan. 12, 2012), All i chern LLC: XP002707617, retrieved from STN Database accession No. 1352926-14-7 see also RN: 135295-74-6; the whole document.
Database Capulus (online) Chemical Abstracts Service Columbus Ohio, 1993, Database accession No. 1994:483155 RN156411-73-3, 156411-74-4 (1993).
Garcia-Gutierrez et al., "Novel inhibitors to Taenia solium Cu/Zn superoxide dismutase identifed by virtual screening" J. Computer. Aided Molecular Design 25:1135-1145 ( 2011).
Gierse et al., "A Novel Autotaxin Inhibitor Reduces Lysophosphatidic Acid Levels in Plasma and the Site of Inflammation" Pharmacol Exp Ther 334:310-317 ( 2010).
Harald M.H.G. Albers et al., "Discovery and Optimization of Boronic Acid Based Inhibitors of Autotaxin" Journal of Medicinal Chemistry 53(13):4958-4967 (Jul. 8, 2010).
Hoeglund et al., "Optimization of a pidemidic acid autotaxin inhibitor" Journal of Medicinal Chemistry 53:1056-1066 (Dec. 30, 2009).
International Search Report for International Patent Application No. PCT/EP2014/075360.
ISR for PCT/EP2013/061890.
ISR for PCT/EP2013/069679.
Jones et al., ACS Med Chem Lett 7:857-861 ( 2016).
Kung et al., "Identification of spirocyclic piperidine-azetidine inverse agonists of the ghrelin receptor" Bioorganic & Medicinal Chemistry Letters (XP028490993), 22(13):4281-4287 (May 8, 2012).
Litherland et al., "The Amino-derivatives of Pentuerythritol. Part I. Preparation." (Published on Jan. 1, 1938. Downloaded by Roche Group on May 24, 2016 17:23:15.),:1588-1595.
Mayo Clinic Staff, (Lupus[online], retrieved from the internet on Jan. 24, 2017; http://www.mayoclinic.org/diseases-conditions/lupus basics/definition/CON-20019676) 2017.
Orr et al., "One-pot synthesis of chiral azetidines from chloroaldehyde and chiral amines" Tetrahedron Letters (XP055073241), 52:3618-3620 ( 2011).
Overberger et al., "Absolute Configuration of 2,7-Diazaspiro[4.4]nonane. A Reassignment" J. Org. Chem. (XP055072840), 46:2757-2764 ( 1981).
Sippy et al., "Preparation and characterization of N-(3-pyridinyl) spirocyclic diamines as ligands for nicotinic acetylcholine receptors" Bioorganic & Medicinal Chemistry Letters 19:1682-1685 ( 2009).
Stocks et al., "A Practical Method for Targeted Library Design Balancing Lead-like Properties with Diversity" Chem Med Chem (XP002707616), 4:800-808 ( 2009).
Written Opinion for PCT/EP2013/061890.
Written Opinion for PCT/EP2013/069679.
Liu, Medicinal Chemistry (English translation),:349 (Aug. 31, 2007).
Tan, Pharmacology (English translation),:27-28 (Jul. 31, 2006).
U.S. Appl. No. 16/793,178, filed Feb. 18, 2020.
U.S. Appl. No. 16/811,656, filed Mar. 6, 2020.
U.S. Appl. No. 16/818,409, filed Mar. 13, 2020.
U.S. Appl. No. 16/832,553, filed Mar. 27, 2020.
U.S. Appl. No. 16/889,322, filed Jun. 1, 2020.
Anderson, "The Process of Structure-Based Drug Design" Chemistry & Biology 10:787-797 (Sep. 2003).
Angeli et al., "Synthesis and carbonic anhydrase inhibition of polycyclic imides moieties" Bioorgan Med Chem 25(20):5373-5379 (Oct. 20, 2017).
Armstrong, J., et al., "Purification and Properties of Human Erythrocyte Carbonic Anhydrases" J Biol Chem 241(21):5137-5149 (Nov. 10, 1966).
Bora, Rajesh O., et al., "[1, 2, 4]-Oxadiazoles: Synthesis and Biological Applications" Mini-Reviews in Med. Chem 14(4):355-369 (Mar. 13, 2014).
Erdik, Ender, "Transition Metal Catalyzed Reactions of Organozinc Reagents" Tetrahedron REP No. 23 48(44):9577-9648 (Jan. 1, 1992).
Farina, V. et al. Organic Reactions "The Stille Reaction" Paquette, Leo A., New York-US:Wiley and Sons, vol. 50:1-704 (Apr. 1, 1997).
Green et al. Protective Groups in Organic Synthesis (Table of Contents only, in 4 pages), Second edition, New York:John Wiley & Sons, Inc., ( 1991).
Hall, Dennis . . . ed. et al. Boronic Acids: Preparation, Applications in Organic Synthesis and Medicine (Description and table of contents only, 2 pages). Hall, Dennis,Wiley,:1-571 (Jan. 1, 2006).
Hemming, K. Science of Synthesis, Product 13: 1, 2, 3-Triazoles "Product Class 6: 1,2,4-Oxadiazoles" Storr. R.C. & Gilchrist, T.L., eds., Stuttgart-DE:Thieme Verlagsgruppe, vol. 13:127-184 (Jan. 1, 2004).
Henke, Brad R., et al., "Optimization of 3-(1H-Indazol-3-ylmethyl)-1,5-benzodiazepines as Potent, Orally Active CCK-A Agonists" J Med Chem 40:2706-2725 (Apr. 22, 1997).
"International Preliminary Report on Patentability—PCT/EP2018/056140":pp. 1-8 (dated Sep. 26, 2019).
"International Search Report—PCT/EP2014/054631":pp. 1-4 (dated Apr. 15, 2014).
"International Search Report—PCT/EP2015/056041":pp. 1-5 (dated May 6, 2015).
"International Search Report—PCT/EP2016/072277":pp. 1-5 (dated Dec. 8, 2016).
"International Search Report—PCT/EP2016/072349":pp. 1-5 (dated Nov. 29, 2016).
"International Search Report—PCT/EP2018/056140":pp. 1-9 (dated May 4, 2018).
"International Search Report—PCT/EP2018/056324":pp. 1-7 (dated May 8, 2018).
"International Search Report—PCT/EP2015/056032":pp. 1-5 (dated Apr. 23, 2015).
"International Search Report—PCT/EP2016/057549":pp. 1-5 (dated Jun. 22, 2016).
"International Search Report—PCT/EP2016/072243":pp. 1-5 (dated Dec. 6, 2016).
"International Search Report—PCT/EP2016/072347":pp. 1-5 (dated Jan. 17, 2017).
"International Search Report—PCT/EP2016/070561":pp. 1-6 (dated Oct. 28, 2016).
Li, Jie Jack et al. Name Reactions for Homologation, Part 1 "Name Reactions for Homologation, Part 1" (Abstract of text, author information and table of contents only, 2 pages),Wiley and Sons,:1-685 (May 1, 2009).
Matralis et al., "Development and therapeutic potential of autotaxin small molecule inhibitors: From bench to advanced clinical trials" Med. Res. Rev.:1-38 ( 2018).

(56) References Cited

OTHER PUBLICATIONS

Mitchell, Terence N., "Palladium-Catalysed Reactions of Organotin Compounds" Synthesis 9:803-815 (Aug. 16, 1991).

Negishi, et al. Metal-Catalyzed Cross-Coupling Reactions "Chapter 1: Palladium or NickelCatalyzed Cross Coupling with Organometals Containing Zinc, Magnesium, Aluminum, and Zirconium" (Preface, table of contents, list of contributors only, 22 pages), Diederich, Francois, Stang, Peter J., eds., Weinheim, DE:Wiley-VCH Verlag GmbH,:1-47 (Jan. 1, 2004).

Polshettiwar, V., et al., "Suzuki-Miyaura Cross-Coupling Reactions in Aqueous Media: Green and Sustainable Syntheses of Biaryls" Chem SUS Chem 3:502-522 (Jan. 1, 2010).

Pouliot, Marie-France, et al., "Synthesis of 1,3,4-oxadiazoles from 1,2-diacylhydrazines using [Et2NSF2]BF4 as a practical cyclodehydration agent" Org. Biomol. Chem 10:988-993 (Oct. 27, 2012).

Schlaeger, E. et al., "The protein hydrolysate, primatone RL, is a cost-effective multiple growth promoter of mammalian cel culture in serum-containing and serum-free medi and displays anti-apoptosis properties" J Immunol Methods 194:191-199 (Apr. 12, 1996).

Stille, John K., "The Palladium-Catalyzed Cross-Coupling Reactions of Organotin Reagents with Organic Electrophiles" Angew Chem. Int. Ed. Engl. 25:508-524 (Jan. 1, 1986).

Suzuki, A., et al., "Palladium-Catalyzed Cross-Coupling Reactions of Organoboron Compounds" Chem Rev. 95:2457-2483 (Jan. 31, 1995).

Suzuki, A., et al., "Recent advances in the cross-coupling reactions of organoboron derivatives with organic electrophiles, 1995-1998" J Organomet Chem 576:147-168 (Jan. 1, 1999).

Suzuki, A., et al., "Synthetic Studies via the cross-coupling reaction of organoboron derivatives with organic halides" Pure Appl Chem 63(3):419-422 (Jan. 1, 1991).

Thiel,, "Structure-aided drug design's next generation" Nat Biotechnol 22(5):513-519 (May 1, 2004).

Tucker, T., et al., "Discovery of 3-{5-[(6-Amino-1H-pyrazolo[3,4-b]pyridine-3-yl)methoxy]-2-chlorophenoxy}-5-chlorobenzonitrile (MK-4965): A Potent, Orally Bioavailable HIV-1 Non-Nucleoside Reverse Transcriptase Inhibitor with Improved Potency against Key Mutant Viruses" J MED CHEM 51:6503-6511 (Jul. 11, 2008).

STN Columbus (STN International) Oct. 9, 2015, pp. 1-13.

Database Registry Numbers, Chemical Abstract Service (CAS), 38 pages ( Dec. 26, 2007).

Harald M.H.G. Albers et al., "Structure-Based Design of Novel Boronic Acid-Based Inhibitors of Autotaxin" Journal of Medicinal Chemistry 54(13):4619-4626 ( 2011).

Patani et al., "Bioisosterism: A Rational Approach in Drug Design," Chem.Ref. (1996), vol. 96, pp. 3147-3176.

Sheridan et al., "Cautious optimism surrounds early clinical data for PD-1 blocker" Nature Biotechnology 30:729-730 ( 2012).

Sheridan et al., "The Most Common Chemical Replacements in Drug-Like Compounds" J. Chem. Inf. Comput. Sci. 42(1):103-108 ( 2002).

\* cited by examiner

OCTAHYDRO-PYRROLO[3,4-C]-PYRROLE DERIVATIVES AND ANALOGS THEREOF AS AUTOTAXIN INHIBITORS

RELATED APPLICATIONS

This application is a continuation of application Ser. No. 14/850,497, filed Sep. 10, 2015, which is a continuation of International Application No. PCT/EP2014/054631, filed Mar. 11, 2014 claiming priority to Application No. EP13158724.8 filed Mar. 12, 2013, each of which are incorporated herein by reference in its entirety.

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

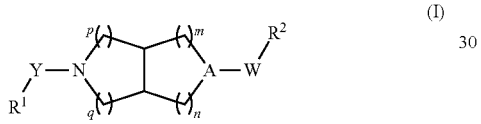

wherein $R^1$ is substituted cycloalkyl, substituted cycloalkylalkyl, substituted phenyl, substituted phenylalkyl, substituted phenoxyalkyl, substituted phenylcycloalkyl, substituted phenylalkenyl, substituted phenylalkynyl, substituted naphthyl, substituted naphthylalkyl, substituted naphthyloxyalkyl, substituted naphthylalkenyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted indolyl, substituted quinolyl, substituted isoquinolyl, substituted 2,3-dihydro-1H-isoindol-2-yl, substituted 1H-indol-2-yl or substituted benzofuran-2-yl wherein substituted cycloalkyl, substituted cycloalkylalkyl, substituted phenyl, substituted phenylalkyl, substituted phenoxyalkyl, substituted phenylcycloalkyl, substituted phenylalkenyl, substituted phenylalkynyl, substituted naphthyl, substituted naphthylalkyl, substituted naphthyloxyalkyl, substituted naphthylalkenyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted indolyl, substituted quinolyl, substituted isoquinolyl, substituted 2,3-dihydro-1H-isoindol-2-yl, substituted 1H-indol-2-yl and substituted benzofuran-2-yl are substituted with $R^7$, $R^8$ and $R^9$;

$R^2$ is substituted phenyl, substituted pyridinyl, substituted pyrrolyl, oxodihydropyridinyl or substituted thiophenyl, wherein substituted phenyl, substituted pyridinyl, substituted pyrrolyl and substituted thiophenyl are substituted with $R^{10}$, $R^{11}$ and $R^{12}$;

Y is —OC(O)—, —NR$^5$C(O)—, —C(O)—, —S(O)$_2$—,

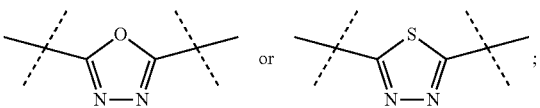

A is —N— or CH—;
W is —O—, —S—, —NR$^6$—, —C(O)—, —S(O)$_2$—, or —CR$^3$R$^4$—;
$R^3$ and $R^4$ are independently selected from H, halogen, alkyl and cycloalkyl;
$R^5$ and $R^6$ are independently selected from H, alkyl and cycloalkyl;
$R^7$, $R^8$ and $R^9$ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, halogen, hydroxy, cyano, alkylsulfanyl, haloalkylsulfanyl, cycloalkylsulfanyl, alkylsulfinyl, haloalkylsulfinyl, cycloalkylsulfinyl, alkylsulfonyl, haloalkylsulfonyl, cycloalkylsulfonyl, substituted aminosulfonyl, substituted amino and substituted aminoalkyl, wherein substituted aminosulfonyl, substituted amino and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl, and wherein substituted phenyl and substituted pyridinyl are optionally substituted with one to three substituents independently selected from alkyl, halogen, haloalkyl, alkoxy and haloalkoxy, wherein at least one of $R^7$, $R^8$ and $R^9$ is not H;
$R^{10}$ is substituted aminosulfonyl, alkoxycarbonyl, alkylcarbonylamino, alkylsulfonylamino, substituted amino, carboxy, cyano, hydroxy or tetrazolyl, wherein substituted amino is substituted on the nitrogen atom with one to two substituents independently selected from H, alkyl, cycloalkyl, cycloalkylalkyl, hydroxyalkyl and alkoxyalkyl;
$R^{11}$ and $R^{12}$ are independently selected from H, alkyl, cycloalkyl, alkoxy, halogen and haloalkyl;
m, n, p and q are independently selected from 1 or 2;
or pharmaceutically acceptable salts.

Autotaxin (ATX) is a secreted enzyme also called ectonucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and—chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include isopropoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group include methoxymethyl, methoxyethyl and isopropoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy or ethoxy. Particular alkoxycarbonyl group include groups of the formula —C(O)—R', wherein R' is methoxy.

The term "alkoxyhaloalkyl" denotes a haloalkyl group wherein at least one of the hydrogen atoms of the haloalkyl group has been replaced by an alkoxy group. Exemplary alkoxyalkyl groups include methoxytrifluoroethyl, ethoxytrifluoroethyl, methoxytrifluoropropyl and ethoxytrifluoropropyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl and sec-butyl, pentyl. Particular alkyl groups include methyl, ethyl, propyl and isopropyl. More particular alkyl group is methyl.

The term "alkylcarbonyl" denotes a group of the formula —C(O)—R', wherein R' is an alkyl group. Examples of alkylcarbonyl groups include groups of the formula —C(O)—R', wherein R' is methyl or ethyl. Particular alkylcarbonyl groups include groups of the formula —C(O)—R', wherein R' is methyl.

The term "alkylcarbonylamino" denotes a group of the formula —NH—C(O)—R', wherein R' is an alkyl group. Examples of alkylcarbonylamino groups include groups of the formula —NH—C(O)—R', wherein R' is methyl or ethyl. Particular a alkylcarbonylamino groups include groups of the formula —NH—C(O)—R', wherein R' is methyl.

The term "alkylsulfanyl" denotes a group of the formula —S—R', wherein R' is an alkyl group. Examples of alkylsulfanyl groups include groups of the formula —S—R', wherein R' is methyl, ethyl, n-propyl, isopropyl, n-butyl, isobutyl or tert-butyl. Particular alkylsulfanyl groups include group of the formula —S—R', wherein R' is methyl.

The term "alkylsulfinyl" denotes a group of the formula —S(O)—R', wherein R' is an alkyl group. Examples of alkylsulfinyl groups include groups of the formula —S(O)—R', wherein R' is methyl, ethyl, n-propyl, isopropyl, n-butyl, isobutyl or tert-butyl. Particular alkylsulfinyl groups include group of the formula —S(O)—R', wherein R' is methyl.

The term "alkylsulfonyl" denotes a group of the formula —S(O)$_2$—R', wherein R' is an alkyl group. Examples of alkylsulfonyl groups include groups of the formula —S(O)$_2$—R', wherein R' is methyl, ethyl, n-propyl, isopropyl, n-butyl, isobutyl or tert-butyl. Particular alkylsulfonyl groups include group of the formula —S(O)$_2$—R', wherein R' is methyl.

The term "alkylsulfonylamino" denotes a group of the formula —NH—S(O)$_2$—R', wherein R' is an alkyl group. Examples of alkylsulfonylamino groups include groups of the formula —NH—S(O)$_2$—R', wherein R' is methyl or ethyl. Particular a alkylsulfonylamino groups include groups of the formula —NH—S(O)$_2$—R', wherein R' is methyl.

The term "amino" denotes a —NH$_2$ group.

The term "aminoalkyl" denotes an alkyl group wherein at least one of the hydrogen atoms of the alkyl group has been replaced by an aminogroup. Examples of aminoalkyl include aminomethyl, aminoethyl, amino-1-methyl-ethyl, aminopropyl, aminomethylpropyl and aminopropyl. Particular examples are aminomethyl and haminoethyl.

The term "aminosulfonyl" denotes a —S(O)$_2$—NH$_2$ group.

The term "carbonyl" denotes a —C(O)— group.

The term "carboxy" denotes a —COOH group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl groups include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl.

Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamantanylmethyl and adamantanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamantanylmethyl and adamantanylethyl. Further particular examples cycloalkylalkyl are cyclohexylmethyl, cyclohexylethyl, bicyclo[4.1.0]heptanylmethyl, bicyclo[2.2.2]octanylmethyl, adamantanylmethyl and adamantanylethyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "cycloalkylsulfanyl" denotes a group of the formula —S—R', wherein R' is a cycloalkyl group. Examples of cycloalkylsulfanyl groups include groups of the formula —S—R', wherein R' is cyclopropyl.

The term "cycloalkylsulfinyl" denotes a group of the formula —S(O)—R', wherein R' is a cycloalkyl group. Examples of cycloalkylsulfinyl groups include groups of the formula —S(O)—R', wherein R' is cyclopropyl.

The term "cycloalkylsulfonyl" denotes a group of the formula —S(O)$_2$—R', wherein R' is a cycloalkyl group. Examples of cycloalkylsulfonyl groups include groups of the formula —S(O)$_2$—R', wherein R' is cyclopropyl.

The term "haloalkoxy" denotes an alkoxy group wherein at least one of the hydrogen atoms of the alkoxy group has been replaced by the same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy group is trifluoromethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "haloalkylsulfanyl" denotes a group of the formula —S—R', wherein R' is a haloalkyl group. Examples of haloalkylsulfanyl groups include groups of the formula —S—R', wherein R' is trifluoromethyl.

The term "haloalkylsulfinyl" denotes a group of the formula —S(O)—R', wherein R' is a haloalkyl group. Examples of haloalkylsulfinyl groups include groups of the formula —S(O)—R', wherein R' is trifluoromethyl.

The term "haloalkylsulfonyl" denotes a group of the formula —S(O)$_2$—R', wherein R' is a haloalkyl group. Examples of haloalkylsulfonyl groups include groups of the formula —S(O)$_2$—R', wherein R' is trifluoromethyl.

The term "halogen" and "halo" are used interchangeably herein and denote fluoro, chloro, bromo, or iodo. Particular halogens are chloro and fluoro.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methyl-ethyl, hydroxypropyl, hydroxymethylpropyl and dihydroxypropyl. Particular examples are hydroxymethyl and hydroxyethyl.

The term "hydroxyhaloalkyl" denotes a haloalkyl group wherein at least one of the hydrogen atoms of the haloalkyl group has been replaced by an hydroxy group. Exemplary hydroxyhaloalkyl groups include hydroxytrifluoroethyl and hydroxytrifluoropropyl. Particular hydroxyhaloalkyl groups include hydroxytrifluoroethyl.

The term "naphthylalkenyl" denotes an alkenyl group wherein at least one of the hydrogen atoms of the alkenyl group has been replaced a naphthynaphthyl. Particular naphthylalkenyl group is naphytylethenyl.

The term "naphthylalkyl" denotes an alkyl group wherein at least one of the hydrogen atoms of the alkyl group has been replaced a naphthyl. Particular naphthylalkyl groups are naphthylmethyl, naphthylethyl and naphthylpropyl.

The term "naphthyloxyalkyl" denotes an alkyl group wherein at least one of the hydrogen atoms of the alkyl group has been replaced by a naphthyloxy group. Exemplary naphthyloxyalkyl groups include naphthyloxymethyl, naphthyloxyethyl and naphthyloxypropyl.

The term "phenoxy" denotes a group of the formula —O—R', wherein R' is a phenyl.

The term "phenoxyalkyl" denotes an alkyl group wherein at least one of the hydrogen atoms of the alkyl group has been replaced by a phenoxy group. Exemplary phenoxyalkyl groups include phenoxymethyl, phenoxyethyl and phenoxypropyl. Particular alkoxyalkyl group is phenoxymethyl.

The term "phenylalkenyl" denotes an alkenyl group wherein at least one of the hydrogen atoms of the alkenyl group has been replaced a phenyl. Particular phenylalkenyl group is phenylethenyl.

The term "phenylalkyl" denotes an alkyl group wherein at least one of the hydrogen atoms of the alkyl group has been replaced a phenyl. Particular phenylalkyl groups are benzyl, phenethyl and phenylpropyl. More particular phenylalkyl groups are benzyl and phenethyl. Further particular phenylalkyl group is benzyl.

The term "phenylalkynyl" denotes an alkynyl group wherein at least one of the hydrogen atoms of the alkynyl group has been replaced a phenyl. Particular phenylalkynyl group is phenylethynyl.

The term "phenylcyloalkyl" denotes a cycloalkyl group wherein at least one of the hydrogen atoms of the cycloalkyl group has been replaced a phenyl. Particular phenylcycloalkyl group is phenylcyclopropyl.

The term "pyridinylalkenyl" denotes an alkenyl group wherein at least one of the hydrogen atoms of the alkenyl group has been replaced a pyridinyl. Particular pyridinylalkenyl group is pyridinylethenyl.

The term "pyridinylalkyl" denotes an alkyl group wherein at least one of the hydrogen atoms of the alkyl group has been replaced a pyridinyl. Particular pyridinylalkyl groups are pyridinylmethyl, pyridinylethyl and pyridinylpropyl. More particular pyridinylalkyl group is pyridinylethyl.

The term "pyridinylalkynyl" denotes an alkynyl group wherein at least one of the hydrogen atoms of the alkynyl group has been replaced a pyridinyl. Particular pyridinylalkynyl group is pyridinylethynyl.

The term "thiophenylalkenyl" denotes an alkenyl group wherein at least one of the hydrogen atoms of the alkenyl group has been replaced a thiophenyl. Particular thiophenylalkenyl group is thiophenylethenyl.

The term "thiophenylalkyl" denotes an alkyl group wherein at least one of the hydrogen atoms of the alkyl group has been replaced a thiophenyl. Particular thiophenylalkyl groups are thiophenylmethyl, thiophenylethyl and thiophenylpropyl. More particular thiophenylalkyl group is thiophenylmethyl.

The term "thiophenylalkynyl" denotes an alkynyl group wherein at least one of the hydrogen atoms of the alkynyl group has been replaced a thiophenyl. Particular thiophenylalkynyl group is thiophenylethynyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the sodium and potassium salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol µM.

The abbreviation uL means microliter and is equivalent to the symbol µL.

The abbreviation ug means microgram and is equivalent to the symbol µg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A further embodiment of the present invention are compounds according to formula (I) as described herein, wherein $R^1$ is substituted phenyl, substituted phenylalkyl, substituted phenylalkenyl, substituted naphthyl, substituted indolyl, substituted quinolyl, or substituted isoquinolyl, wherein substituted phenyl, substituted phenylalkyl, substituted phenylalkenyl, substituted naphthyl, substituted indolyl, substituted quinolyl and substituted isoquinolyl are substituted with $R^7$, $R^8$ and $R^9$.

A particular embodiment of the present invention are compounds according to formula (I) as described herein, wherein $R^1$ is phenylalkyl substituted with $R^7$, $R^8$ and $R^9$.

In a further embodiment of the present invention are compounds according to formula (I) as described herein, wherein $R^1$ is 3,5-dichlorobenzyl, 4-trifluoromethoxybenzyl or 4-trifluoromethoxyphenylethyl.

The present invention also relates to compounds according to formula (I) as described herein, wherein $R^1$ is substituted phenyl or substituted pyridinyl, wherein substituted phenyl and substituted pyridinyl are substituted with $R^{10}$, $R^{11}$ and $R^{12}$.

A further particular embodiment of the present invention are compounds according to formula (I) as described herein, wherein $R^2$ is phenyl substituted phenyl with $R^{10}$, $R^{11}$ and $R^{12}$.

Another further embodiment of the present invention are compounds according to formula (I) as described herein, wherein $R^2$ is 4-aminosulfonylphenyl, 3-fluoro-4-aminosulfonylphenyl, 3-aminosulfonylpyridin-6-yl or 2-aminosulfonylpyridin-5-yl.

Another embodiment of the present invention are compounds according to formula (I) as described herein, wherein Y is —OC(O)— or —C(O)—.

A more particular embodiment of the present invention are compounds according to formula (I) as described herein, wherein A is —N—.

Also an embodiment of the present invention are compounds according to formula (I) as described herein, wherein W is —C(O)— or —S(O)$_2$—.

Another embodiment of the present invention are compounds according to formula (I) as described herein, wherein W is —C(O)—.

Another embodiment of the present invention are compounds according to formula (I) as described herein, wherein $R^7$, $R^8$ and $R^9$ are independently selected from H, alkoxy, haloalkoxy, halogen, alkylsulfonyl and phenyl substituted with one halogen, and wherein at least one of $R^7$, $R^8$ and $R^9$ is not H.

A further particular embodiment of the present invention are compounds according to formula (I) as described herein, wherein $R^7$ is alkoxy, haloalkoxy, halogen or phenyl substituted with one halogen.

A further particular embodiment of the present invention are compounds according to formula (I) as described herein, wherein $R^7$ is haloalkoxy or halogen.

A further particular embodiment of the present invention are compounds according to formula (I) as described herein, wherein $R^8$ is H, halogen or alkylsulfonyl.

A further particular embodiment of the present invention are compounds according to formula (I) as described herein, wherein $R^8$ is H or halogen.

A further particular embodiment of the present invention are compounds according to formula (I) as described herein, wherein $R^9$ is H.

A further particular embodiment of the present invention are compounds according to formula (I) as described herein, wherein $R^{10}$ is aminosulfonyl.

A further particular embodiment of the present invention are compounds according to formula (I) as described herein, wherein $R^{11}$ and $R^{12}$ are independently selected from H, alkyl and halogen.

A further particular embodiment of the present invention are compounds according to formula (I) as described herein, wherein $R^{11}$ and $R^{12}$ are independently selected from H and halogen.

A further particular embodiment of the present invention are compounds according to formula (I) as described herein, wherein m and n are 1.

A further particular embodiment of the present invention are compounds according to formula (I) as described herein, wherein m, n, p and q are 1.

A further particular embodiment of the present invention are compounds according to formula (I) as described herein, wherein $R^2$ is 4-aminosulfonylphenyl and of formula (Ia).

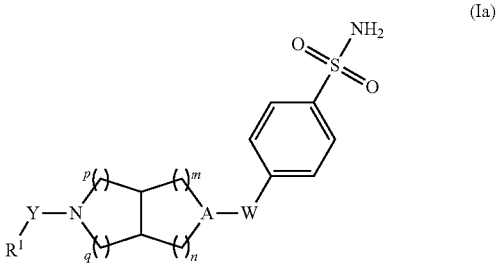

(Ia)

Particular examples of compounds of formula (I) as described herein are selected from (3aR,6aS)-3,5-dichlorobenzyl 5-(4-(N-methylsulfamoyl)benzoyl)hexahydropyrrolo[3,4-c]pyrrole-2(1H)-carboxylate;
(3aR,6aS)-3,5-dichlorobenzyl 5-(5-hydroxypicolinoyl)hexahydropyrrolo[3,4-c]pyrrole-2(1H)-carboxylate;
(3aR,6aS)-3,5-dichlorobenzyl 5-(4-hydroxybenzoyl)hexahydropyrrolo[3,4-c]pyrrole-2(1H)-carboxylate;
trans-3,5-dichlorobenzyl 2-(4-sulfamoylbenzoyl)hexahydro-1H-pyrrolo[3,4-c]pyridine-5(6H)-carboxylate;
(3aR,6aS)-3,5-dichlorobenzyl 5-(5-sulfamoylthiophene-2-carbonyl)hexahydropyrrolo[3,4-c]pyrrole-2(1H)-carboxylate;
(3aR,6aS)-3,5-dichlorobenzyl 5-(4-sulfamoylbenzoyl)hexahydropyrrolo[3,4-c]pyrrole-2(1H)-carboxylate;
(3aR,6aS)-3,5-dichlorobenzyl 5-(4-aminobenzoyl)hexahydropyrrolo[3,4-c]pyrrole-2(1H)-carboxylate;
(3aR,6aS)-3,5-dichlorobenzyl 5-(5-aminopicolinoyl)hexahydropyrrolo[3,4-c]pyrrole-2(1H)-carboxylate;
(3aR,6aS)-3,5-dichlorobenzyl 5-(4-cyanobenzoyl)hexahydropyrrolo[3,4-c]pyrrole-2(1H)-carboxylate;
(3aR,6aS)-3,5-dichlorobenzyl 5-(4-(methoxycarbonyl)benzoyl)hexahydropyrrolo[3,4-c]pyrrole-2(1H)-carboxylate;
4-{(3aS,8aR)-6-[(E)-3-(4-trifluoromethoxy-phenyl)-acryloyl]-octahydro-pyrrolo[3,4-d]azepine-2-carbonyl}-benzenesulfonamide;
(3aS,6aS)-5-(3-fluoro-4-sulfamoyl-benzoyl)-hexahydro-pyrrolo[3,4-c]pyrrole-2-carboxylic acid 4-trifluoromethoxy-benzyl ester;
(3aS,6aS)-5-(6-oxo-1,6-dihydro-pyridine-3-carbonyl)-hexahydro-pyrrolo[3,4-c]pyrrole-2-carboxylic acid 4-trifluoromethoxy-benzyl ester;
(3aS,6aS)-5-(5-sulfamoyl-pyridine-2-carbonyl)-hexahydro-pyrrolo[3,4-c]pyrrole-2-carboxylic acid 4-trifluoromethoxy-benzyl ester;
(3aS,6aS)-5-(1-methyl-4-sulfamoyl-1H-pyrrole-2-carbonyl)-hexahydro-pyrrolo[3,4-c]pyrrole-2-carboxylic acid 4-trifluoromethoxy-benzyl ester;
(3aS,6aS)-5-(1-methyl-5-sulfamoyl-1H-pyrrole-2-carbonyl)-hexahydro-pyrrolo[3,4-c]pyrrole-2-carboxylic acid 4-trifluoromethoxy-benzyl ester;
(3aS,6aS)-5-(6-sulfamoyl-pyridine-3-carbonyl)-hexahydro-pyrrolo[3,4-c]pyrrole-2-carboxylic acid 4-trifluoromethoxy-benzyl ester;
(3aS,6aS)-5-(5-hydroxy-pyridine-2-carbonyl)-hexahydro-pyrrolo[3,4-c]pyrrole-2-carboxylic acid 4-trifluoromethoxy benzyl ester;
(3aS,6aS)-5-(4-hydroxy-benzoyl)-hexahydro-pyrrolo[3,4-c]pyrrole-2-carboxylic acid 4-trifluoromethoxy-benzyl ester;
(3aR,6aS)-3,5-dichlorobenzyl 5-(4-acetamidobenzoyl)hexahydropyrrolo[3,4-c]pyrrole-2(1H)-carboxylate;
(3aR,6aS)-3,5-dichlorobenzyl 5-(5-acetamidopicolinoyl)hexahydropyrrolo[3,4-c]pyrrole-2(1H)-carboxylate;
(3aR,6aS)-3,5-dichlorobenzyl 5-(4-sulfamoylphenylsulfonyl)hexahydropyrrolo[3,4-c]pyrrole-2(1H)-carboxylate;
(3aR,6aS)-3,5-dichlorobenzyl 5-(4-(1H-tetrazol-5-yl)benzoyl)hexahydropyrrolo[3,4-c]pyrrole-2(1H)-carboxylate;
4-((3aR,6aS)-5-((3,5-dichlorobenzyloxy)carbonyl)octahydropyrrolo[3,4-c]pyrrole-2-carbonyl)benzoic acid;
(3aR,6aS)-3,5-dichlorobenzyl 5-(5-(methylsulfonamido)picolinoyl)hexahydropyrrolo[3,4-c]pyrrole-2(1H)-carboxylate;
(3aS,6aS)-5-(4-sulfamoyl-benzoyl)-hexahydro-pyrrolo[3,4-c]pyrrole-2-carboxylic acid 3-chloro-5-methanesulfonyl-benzyl ester;
(3aR,6aS)-5-(4-sulfamoyl-benzoyl)-hexahydro-pyrrolo[3,4-c]pyrrole-2-carboxylic acid 2-fluoro-4-trifluoromethoxy-benzyl ester;
(3aR,6aS)-5-(4-sulfamoyl-benzoyl)-hexahydro-pyrrolo[3,4-c]pyrrole-2-carboxylic acid 4-trifluoromethoxy-benzyl ester;
(3aS,6aS)-5-(4-sulfamoyl-benzoyl)-hexahydro-pyrrolo[3,4-c]pyrrole-2-carboxylic acid 4-trifluoromethoxy-benzyl ester;
4-{(3aR,6aR)-5-[3-(4-trifluoromethoxy-phenyl)-propionyl]-hexahydro-pyrrolo[3,4-c]pyrrole-2-carbonyl}-benzenesulfonamide;
4-{(3aR,6aR)-5-[(E)-3-(4-trifluoromethoxy-phenyl)-acryloyl]-hexahydro-pyrrolo[3,4-c]pyrrole-2-carbonyl}-benzenesulfonamide;
4-[(3aR,6aS)-5-(4-isopropoxy-naphthalene-2-carbonyl)-hexahydro-pyrrolo[3,4-c]pyrrole-2-carbonyl]-benzenesulfonamide;
4-{(3aR,6aS)-5-[1-(2,2,2-trifluoro-ethoxy)-isoquinoline-3-carbonyl]-hexahydro-pyrrolo[3,4-c]pyrrole-2-carbonyl}-benzenesulfonamide;
4-[(3aR,6aS)-5-(1-Methyl-5-trifluoromethoxy-1H-indole-2-carbonyl)-hexahydro-pyrrolo[3,4-c]pyrrole-2-carbonyl]-benzenesulfonamide;
4-[(3aR,6aS)-5-(4-Isopropoxy-quinoline-2-carbonyl)-hexahydro-pyrrolo[3,4-c]pyrrole-2-carbonyl]-benzenesulfonamide;
4-[(3aS,6aR)-5-(4'-chloro-biphenyl-4-carbonyl)-hexahydro-pyrrolo[3,4-c]pyrrole-2-carbonyl]-benzenesulfonamide;
4-{(3aS,6aR)-5-[3-(2-fluoro-4-trifluoromethoxy-phenyl)-propionyl]-hexahydro-pyrrolo[3,4-c]pyrrole-2-carbonyl}-benzenesulfonamide;
4-{(3aS,6aR)-5-[3-(4-trifluoromethoxy-phenyl)-propionyl]-hexahydro-pyrrolo[3,4-c]pyrrole-2-carbonyl}-benzenesulfonamide;
4-((3aR,6aR)-5-(3-(2-fluoro-4-(trifluoromethoxy)phenyl)propanoyl)octahydropyrrolo[3,4-c]pyrrole-2-carbonyl)benzenesulfonamide;
(+)-trans-3,5-dichlorobenzyl 2-(4-sulfamoylbenzoyl)hexahydro-1H-pyrrolo[3,4-c]pyridine-5(6H)-carboxylate;
(−)-trans-3,5-dichlorobenzyl 2-(4-sulfamoylbenzoyl)hexahydro-1H-pyrrolo[3,4-c]pyridine-5(6H)-carboxylate;
and pharmaceutically acceptable salts thereof.

Also particular examples of compounds of formula (I) as described herein are selected from
(3aR,6aS)-3,5-dichlorobenzyl 5-(4-(N-methylsulfamoyl)benzoyl)hexahydropyrrolo[3,4-c]pyrrole-2(1H)-carboxylate;
(3aR,6aS)-3,5-dichlorobenzyl 5-(5-hydroxypicolinoyl)hexahydropyrrolo[3,4-c]pyrrole-2(1H)-carboxylate;
(3aR,6aS)-3,5-dichlorobenzyl 5-(4-hydroxybenzoyl)hexahydropyrrolo[3,4-c]pyrrole-2(1H)-carboxylate;
trans-3,5-dichlorobenzyl 2-(4-sulfamoylbenzoyl)hexahydro-1H-pyrrolo[3,4-c]pyridine-5(6H)-carboxylate;
(3aR,6aS)-3,5-dichlorobenzyl 5-(5-sulfamoylthiophene-2-carbonyl)hexahydropyrrolo[3,4-c]pyrrole-2(1H)-carboxylate;
(3aR,6aS)-3,5-dichlorobenzyl 5-(4-sulfamoylbenzoyl)hexahydropyrrolo[3,4-c]pyrrole-2(1H)-carboxylate;
(3aR,6aS)-3,5-dichlorobenzyl 5-(4-aminobenzoyl)hexahydropyrrolo[3,4-c]pyrrole-2(1H)-carboxylate;
(3aR,6aS)-3,5-dichlorobenzyl 5-(5-aminopicolinoyl)hexahydropyrrolo[3,4-c]pyrrole-2(1H)-carboxylate;
(3aR,6aS)-3,5-dichlorobenzyl 5-(4-cyanobenzoyl)hexahydropyrrolo[3,4-c]pyrrole-2(1H)-carboxylate;

(3aR,6aS)-3,5-dichlorobenzyl 5-(4-(methoxycarbonyl)benzoyl)hexahydropyrrolo[3,4-c]pyrrole-2(1H)-carboxylate;
4-{(3aS,8aR)-6-[(E)-3-(4-trifluoromethoxy-phenyl)-acryloyl]-octahydro-pyrrolo[3,4-d]azepine-2-carbonyl}-benzenesulfonamide;
(3aS,6aS)-5-(3-fluoro-4-sulfamoyl-benzoyl)-hexahydropyrrolo[3,4-c]pyrrole-2-carboxylic acid 4-trifluoromethoxy-benzyl ester;
(3aS,6aS)-5-(6-oxo-1,6-dihydro-pyridine-3-carbonyl)-hexahydro-pyrrolo[3,4-c]pyrrole-2-carboxylic acid 4-trifluoromethoxy-benzyl ester;
(3aS,6aS)-5-(5-sulfamoyl-pyridine-2-carbonyl)-hexahydropyrrolo[3,4-c]pyrrole-2-carboxylic acid 4-trifluoromethoxy-benzyl ester;
(3aS,6aS)-5-(1-methyl-4-sulfamoyl-1H-pyrrole-2-carbonyl)-hexahydro-pyrrolo[3,4-c]pyrrole-2-carboxylic acid 4-trifluoromethoxy-benzyl ester;
(3aS,6aS)-5-(1-methyl-5-sulfamoyl-1H-pyrrole-2-carbonyl)-hexahydro-pyrrolo[3,4-c]pyrrole-2-carboxylic acid 4-trifluoromethoxy-benzyl ester;
(3aS,6aS)-5-(6-sulfamoyl-pyridine-3-carbonyl)-hexahydropyrrolo[3,4-c]pyrrole-2-carboxylic acid 4-trifluoromethoxy-benzyl ester;
(3aS,6aS)-5-(5-hydroxy-pyridine-2-carbonyl)-hexahydropyrrolo[3,4-c]pyrrole-2-carboxylic acid 4-trifluoromethoxy benzyl ester;
(3aS,6aS)-5-(4-hydroxy-benzoyl)-hexahydro-pyrrolo[3,4-c]pyrrole-2-carboxylic acid 4-trifluoromethoxy-benzyl ester;
(3aR,6aS)-3,5-dichlorobenzyl 5-(4-acetamidobenzoyl)hexahydropyrrolo[3,4-c]pyrrole-2(1H)-carboxylate;
(3aR,6aS)-3,5-dichlorobenzyl 5-(5-acetamidopicolinoyl)hexahydropyrrolo[3,4-c]pyrrole-2(1H)-carboxylate;
(3aR,6aS)-3,5-dichlorobenzyl 5-(4-sulfamoylphenylsulfonyl)hexahydropyrrolo[3,4-c]pyrrole-2(1H)-carboxylate;
(3aR,6aS)-3,5-dichlorobenzyl 5-(4-(1H-tetrazol-5-yl)benzoyl)hexahydropyrrolo[3,4-c]pyrrole-2(1H)-carboxylate;
4-((3aR,6aS)-5-((3,5-dichlorobenzyloxy)carbonyl)octahydropyrrolo[3,4-c]pyrrole-2-carbonyl)benzoic acid;
(3aR,6aS)-3,5-dichlorobenzyl 5-(5-(methylsulfonamido)picolinoyl)hexahydropyrrolo[3,4-c]pyrrole-2(1H)-carboxylate;
(3aS,6aS)-5-(4-sulfamoyl-benzoyl)-hexahydro-pyrrolo[3,4-c]pyrrole-2-carboxylic acid 3-chloro-5-methanesulfonyl-benzyl ester;
(3aR,6aS)-5-(4-sulfamoyl-benzoyl)-hexahydro-pyrrolo[3,4-c]pyrrole-2-carboxylic acid 2-fluoro-4-trifluoromethoxy-benzyl ester;
(3aR,6aS)-5-(4-sulfamoyl-benzoyl)-hexahydro-pyrrolo[3,4-c]pyrrole-2-carboxylic acid 4-trifluoromethoxy-benzyl ester;
(3aS,6aS)-5-(4-sulfamoyl-benzoyl)-hexahydro-pyrrolo[3,4-c]pyrrole-2-carboxylic acid 4-trifluoromethoxy-benzyl ester;
4-{(3aR,6aR)-5-[3-(4-trifluoromethoxy-phenyl)-propionyl]-hexahydro-pyrrolo[3,4-c]pyrrole-2-carbonyl}-benzenesulfonamide;
4-{(3aR,6aR)-5-[(E)-3-(4-trifluoromethoxy-phenyl)-acryloyl]-hexahydro-pyrrolo[3,4-c]pyrrole-2-carbonyl}-benzenesulfonamide;
4-[(3aR,6aS)-5-(4-isopropoxy-naphthalene-2-carbonyl)-hexahydro-pyrrolo[3,4-c]pyrrole-2-carbonyl]-benzenesulfonamide;
4-{(3aR,6aS)-5-[1-(2,2,2-trifluoro-ethoxy)-isoquinoline-3-carbonyl]-hexahydro-pyrrolo[3,4-c]pyrrole-2-carbonyl}-benzenesulfonamide;
4-[(3aR,6aS)-5-(1-Methyl-5-trifluoromethoxy-1H-indole-2-carbonyl)-hexahydro-pyrrolo[3,4-c]pyrrole-2-carbonyl]-benzenesulfonamide;
4-[(3aR,6aS)-5-(4-Isopropoxy-quinoline-2-carbonyl)-hexahydro-pyrrolo[3,4-c]pyrrole-2-carbonyl]-benzenesulfonamide;
4-[(3aS,6aR)-5-(4'-chloro-biphenyl-4-carbonyl)-hexahydro-pyrrolo[3,4-c]pyrrole-2-carbonyl]-benzenesulfonamide;
4-{(3aS,6aR)-5-[3-(2-fluoro-4-trifluoromethoxy-phenyl)-propionyl]-hexahydro-pyrrolo[3,4-c]pyrrole-2-carbonyl}-benzenesulfonamide;
4-{(3aS,6aR)-5-[3-(4-trifluoromethoxy-phenyl)-propionyl]-hexahydro-pyrrolo[3,4-c]pyrrole-2-carbonyl}-benzenesulfonamide;
4-((3aR,6aR)-5-(3-(2-fluoro-4-(trifluoromethoxy)phenyl)propanoyl)octahydropyrrol[3,4-c]pyrrole-2-carbonyl)benzenesulfonamide;
(+)-trans-3,5-dichlorobenzyl 2-(4-sulfamoylbenzoyl)hexahydro-1H-pyrrolo[3,4-c]pyridine-5(6H)-carboxylate;
(−)-trans-3,5-dichlorobenzyl 2-(4-sulfamoylbenzoyl)hexahydro-1H-pyrrolo[3,4-c]pyridine-5(6H)-carboxylate;
(3aS,6aS)-5-(2-fluoro-4-sulfamoyl-benzoyl)-hexahydropyrrolo[3,4-c]pyrrole-2-carboxylic acid 4-trifluoromethoxy-benzyl ester;
5-{(3aR,6aR)-5-[3-(4-trifluoromethoxy-phenyl)-propionyl]-hexahydro-pyrrolo[3,4-c]pyrrole-2-carbonyl}-pyridine-2-sulfonic acid amide;
5-((3aS,6aS)-5-(4-ethoxyquinoline-2-carbonyl)octahydropyrrolo[3,4-c]pyrrole-2-carbonyl)pyridine-2-sulfonamide;
(3aS,6aS)-5-(3-fluoro-4-sulfamoyl-benzoyl)-hexahydropyrrolo[3,4-c]pyrrole-2-carboxylic acid 4-cyano-2-(2,2-dimethyl-propionylamino)-benzyl ester;
(3aS,6aS)-5-(6-sulfamoyl-pyridine-3-carbonyl)-hexahydropyrrolo[3,4-c]pyrrole-2-carboxylic acid 4-cyano-2-(2,2-dimethyl-propionylamino)-benzyl ester;
(3aS,6aS)-5-(4-sulfamoyl-benzoyl)-hexahydro-pyrrolo[3,4-c]pyrrole-2-carboxylic acid 4-cyano-2-(2,2-dimethyl-propionylamino)-benzylester;
(3aS,6aS)-5-(2-fluoro-4-sulfamoyl-benzoyl)-hexahydropyrrolo[3,4-c]pyrrole-2-carboxylic acid 4-cyano-2-(2,2-dimethyl-propionylamino)-benzyl ester;
(3aS,6aS)-5-(5-sulfamoyl-pyridine-2-carbonyl)-hexahydropyrrolo[3,4-c]pyrrole-2-carboxylic acid 4-cyano-2-(2,2-dimethyl-propionylamino)-benzyl ester; and
pharmaceutically acceptable salts thereof.

Further particular examples of compounds of formula (I) as described herein are selected from
(3aR,6aS)-3,5-dichlorobenzyl 5-(4-sulfamoylbenzoyl)hexahydropyrrolo[3,4-c]pyrrole-2(1H)-carboxylate;
(3aS,6aS)-5-(3-fluoro-4-sulfamoyl-benzoyl)-hexahydropyrrolo[3,4-c]pyrrole-2-carboxylic acid 4-trifluoromethoxy-benzyl ester;
(3aS,6aS)-5-(5-sulfamoyl-pyridine-2-carbonyl)-hexahydropyrrolo[3,4-c]pyrrole-2-carboxylic acid 4-trifluoromethoxy-benzyl ester;
(3aS,6aS)-5-(6-sulfamoyl-pyridine-3-carbonyl)-hexahydropyrrolo[3,4-c]pyrrole-2-carboxylic acid 4-trifluoromethoxy-benzyl ester;
(3aS,6aS)-5-(4-sulfamoyl-benzoyl)-hexahydro-pyrrolo[3,4-c]pyrrole-2-carboxylic acid 4-trifluoromethoxy-benzyl ester;
4-{(3aR,6aR)-5-[3-(4-trifluoromethoxy-phenyl)-propionyl]-hexahydro-pyrrolo[3,4-c]pyrrole-2-carbonyl}-benzenesulfonamide;
and pharmaceutically acceptable salts thereof.

Also further particular examples of compounds of formula (I) as described herein are selected from (3aR,6aS)-3,5-dichlorobenzyl 5-(4-sulfamoylbenzoyl)hexahydropyrrolo[3,4-c]pyrrole-2(1H)-carboxylate;

(3aS,6aS)-5-(3-fluoro-4-sulfamoyl-benzoyl)-hexahydropyrrolo[3,4-c]pyrrole-2-carboxylic acid 4-trifluoromethoxy-benzyl ester;

(3aS,6aS)-5-(5-sulfamoyl-pyridine-2-carbonyl)-hexahydropyrrolo[3,4-c]pyrrole-2-carboxylic acid 4-trifluoromethoxy-benzyl ester;

(3aS,6aS)-5-(6-sulfamoyl-pyridine-3-carbonyl)-hexahydropyrrolo[3,4-c]pyrrole-2-carboxylic acid 4-trifluoromethoxy-benzyl ester;

(3aS,6aS)-5-(4-sulfamoyl-benzoyl)-hexahydro-pyrrolo[3,4-c]pyrrole-2-carboxylic acid 4-trifluoromethoxy-benzyl ester;

4-{(3aR,6aR)-5-[3-(4-trifluoromethoxy-phenyl)-propionyl]-hexahydro-pyrrolo[3,4-c]pyrrole-2-carbonyl}-benzenesulfonamide;

(3aS,6aS)-5-(5-sulfamoyl-pyridine-2-carbonyl)-hexahydropyrrolo[3,4-c]pyrrole-2-carboxylic acid 4-cyano-2-(2,2-dimethyl-propionylamino)-benzyl ester;

and pharmaceutically acceptable salts thereof. Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

Compounds of general formula (I) can be synthesised from amine precursor 1 and appropriate reagents, using methods well known in the art.

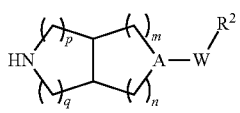

1

For instance, amine 1 is reacted with a suitable chloroformate ester of formula $R^1$—O—C(O)—Cl (2), or with an imidazole-1-carboxylate ester of formula (3), leading to a compound of formula (I) wherein Y is —OC(O)—.

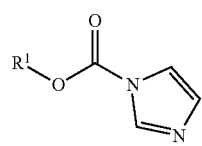

3

The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Chloroformate esters 2 are commercially available or can be synthesised from the corresponding alcohol of formula $R^1$—OH, by reaction with phosgene or a phosgene equivalent (e. g., diphosgene, triphosgene), as described in the literature.

Imidazole-1-carboxylate esters 3 are synthesised from the corresponding alcohols of formula $R^1$—OH, by reaction with 1,1'-carbonyldiimidazole. The reaction is performed at room temperature, in a solvent such as dichloromethane, tetrahydrofuran or acetonitrile. The imidazole-1-carboxylate esters 3 are typically not isolated but directly reacted with amines 1 as described above.

Alcohols of formula $R^1$—OH are commercially available or can be produced by methods described herein or known in the art.

Alternatively, amine 1 is reacted with a suitable N-(chlorocarbonyl)amine of formula $R^1$—N($R^5$)—C(O)—Cl (4), or, in the case where $R^5$ is H, with an isocyanate of formula $R^1$—NCO (5), leading to compounds of formula (I) wherein Y is —N$R^5$C(O)—.

N-(Chlorocarbonyl)amines (4) are synthesised from the corresponding amines of formula $R^1$—N($R^5$)H by reaction with phosgene or a phosgene equivalent, as described in the literature.

Isocyanates 5 are commercially available or can be prepared from the corresponding amines of formula $R^1$—$NH_2$, by reaction with phosgene or a phosgene equivalent (e. g., diphosgene, triphosgene, 1,1'-carbonyldiimidazole) using conditions described in the literature.

Alternatively, amine 1 is reacted with a suitable carboxylic acid of formula $R^1$—COOH (6) leading to a compound of formula (I), wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1 can also be reacted with suitable acylating reagents such as acyl chlorides of formula $R^1$—COCl (7) to lead to compounds of formula (I) wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Carboxylic acids (6) and acyl halides (7) are commercially available or can be prepared as described herein or in the literature.

Alternatively, amine 1 is reacted with a suitable sulfonyl chloride of formula $R^1$—$SO_2$Cl (8), leading to compounds of formula (I) wherein Y is —S($O_2$)—. The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Sulfonyl chlorides (8) are commercially available or can be synthesised as described herein or in the literature.

Alternatively, amine 1 is reacted with a suitable chloro-oxadiazole reagent of general formula 9, or with oxadiazolone reagent 10, leading to a compound of formula (I), wherein Y is

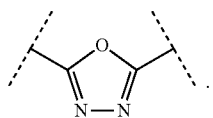

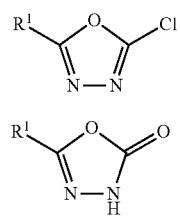

In the case where compounds of formula (I) are produced from amine 1 and chloro-oxadiazole 9, the reaction is performed in the presence of a base, e. g., potassium carbonate, triethylamine, or 1,8-diazabicyclo[5.4.0]undec-7-ene, in a solvent such as toluene, ethanol, N,N-dimethylformamide, or 1,4-dioxane at temperatures between 20° C. and 150° C.

In the case where compounds of formula (I) are produced from amine 1 and oxadiazolone 10, the reaction is performed in the presence of a coupling agent, e. g. benzotriazol-1-yl-oxy-tris-(dimethylamino)-phosphonium hexafluorophosphate and a base, e. g., diisopropylethylamine or 4-methylmorpholine, in a solvent such as N,N-dimethylformamide, at temperatures between 20° C. and 100° C. as described in the literature.

Oxadiazolones 10 are commercially available or can be produced as described in the literature.

Chloro-oxadiazoles 9 are commercially available or can be produced from the corresponding oxadiazolones, by reaction with a suitable halogenating reagent, e. g. phosphorus oxychloride and/or phosphorus pentachloride, at temperatures between 60° C. and 120° C.

Alternatively, amine 1 is reacted with a suitable halo-thiadiazole reagent of general formula 11 (X=Cl or Br), or with thiadiazolethione reagent 12, leading to compounds of (I) wherein Y is

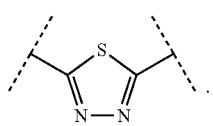

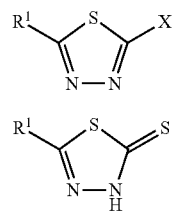

In the case where compounds of formula (I) are produced from amine 1 and halo-thiadiazole 11, the reaction is performed in the presence of a base, e. g. potassium carbonate, triethylamine or 1,8-diazabicyclo[5.4.0]undec-7-ene, in a solvent such as toluene, ethanol, N,N-dimethylformamide or 1,4-dioxane, at temperatures between 20° C. and 150° C.

In the case where compounds of formula (I) are produced from amine 1 and thiadiazolethione 12, the reaction is performed in a solvent such as ethanol or N,N-dimethylformamide at temperatures between 20° C. and 100° C. as described in the literature.

Thiadiazolethiones 12 are commercially available or can be produced as described in the literature.

Halo-thiadiazoles 11 are commercially available or can be produced as described in the literature.

Amines of general formula 1 are synthesised from suitably protected precursors 13.

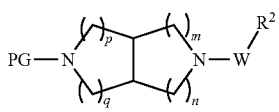

Suitable protective groups (PG) are tert-butoxycarbonyl, benzyloxycarbonyl and substituted benzyloxycarbonyl such as 3,5-dichloro benzyloxycarbonyl. The deprotection of intermediates 13 can be performed using methods and reagents known in the art.

For instance, in the case where PG is optionally substituted benzyloxycarbonyl, the deprotection may be performed by hydrogenation at pressures between 1 bar and 100 bar, in the presence of a suitable catalyst such as palladium on activated charcoal, at temperatures between 20° C. and 150° C. in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane at temperatures between 0° C. and 30° C.

Intermediates 13, wherein A is N are represented by general structure 13A.

PG is a suitable protective group, e. g., tert-butoxycarbonyl, benzyloxycarbonyl and substituted benzyloxycarbonyl such as 3,5-dichloro benzyloxycarbonyl.

Intermediates 13A can be produced from amine precursors of general formula 14 by reaction with appropriate reagents, using methods known in the art.

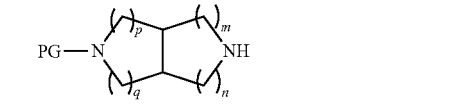

14

For instance, 14 is reacted with alkylating agents of general formula X—CR$^3$R$^4$—R$^2$ (15) where X is a leaving group such as Cl, Br, I, or OSO$_2$CH$_3$, leading to 13A, wherein W is —CR$^3$R$^4$—. This reaction is performed in a solvent such as tetrahydrofuran or N,N-dimethylformamide, in the presence of a base, e. g. triethylamine or potassium carbonate, at temperatures between 0° C. and 100° C.

Alternatively, for compounds of formula 13A, wherein W is —CR$^3$R$^4$—, R$^4$ is hydrogen, alkyl or cycloalkyl, and R$^3$ is H, amine 14 is reacted with aldehydes or ketones of general formula R$^4$—C(O)—R$^2$ (16) in a reductive amination reaction, leading to 13A. This reaction is performed in the presence of a suitable reducing agent, e. g., sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 14 is reacted with a suitable carboxylic acid of formula R$^2$—COOH (17), leading to compounds of formula 13A, wherein W is —C(O)—. The reaction is performed in the presence of a coupling agent such as 1,1'-carbonyldiimidazole, N,N'-di cyclohexylcarbodiimide, 1-(3-dimethylaminopropyl)-3-ethyl-carbodiimide hydrochloride, 0-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, amine 14 is reacted with a suitable sulfonyl chloride of formula R$^2$—SO$_2$Cl (18), leading to compounds of formula 13A, wherein W is —S(O$_2$)—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Amines 14, alkylating agents 15, aldehydes/ketones 16, carboxylic acids 17, sulfonyl chlorides 18, and amines 22 are commercially available or can be synthesised as described in the literature or in the experimental section.

Intermediates 13 wherein A is C—H are represented by general formula 13B, wherein PG is a suitable protective group, e. g tert-butoxycarbonyl, benzyloxycarbonyl and substituted benzyloxycarbonyl such as 3,5-dichloro benzyloxycarbonyl.

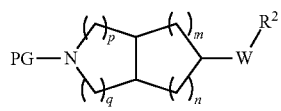

13B

Compound 13B, wherein W is —NR$^6$—, is produced from ketone 19 by reaction with an amine of formula HN(R$^6$)R$^2$ (20) in the presence of a suitable reducing agent, e. g. sodium borohydride or sodium triacetoxyborohydride, in a solvent such as methanol, acetic acid, tetrahydrofuran, 1,2-dichloroethane, or mixtures thereof, at temperatures between 0° C. and 50° C.

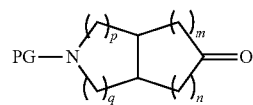

19

Ketones 19 and amines 20 are commercially available or can be prepared as described in the literature.

Compound 13B, wherein W is —O— or —S—, is produced from alcohol 21 using methods and reagents known in the art.

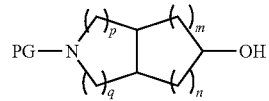

21

For instance, alcohol 24 is reacted at room temperature with phenol HO—R$^2$ or thiophenol HS—R$^2$ in the presence of triphenylphosphine and an dialkylazodicarboxylate, e. g. diisopropylazodicarboxylate or diethylazodicarboxylate, in a solvent such as toluene, dichloromethane, or tetrahydrofuran, leading to 13B, wherein W is —O— or —S—.

Alternatively, conversion of alcohol 21 to the corresponding methanesulfonate using methanesulfonyl chloride in the presence of a base, e. g. triethylamine, in a solvent such as dichloromethane or tetrahydrofuran, at temperatures between −20° C. and +30° C., and treatment of the methanesulfonate intermediate with phenol HO—R$^2$ or thiophenol HS—R$^2$ in the presence of a base, e. g., potassium carbonate, in a solvent such as N,N-dimethylformamide or acetonitrile, at temperatures between 20° C. and 100° C., leads to 13B, wherein W is —O— or —S—.

Compound 13B, wherein W is —SO$_2$—, is produced from compound 13B, wherein W is —S—, by oxidation with a suitable reagent, e. g., hydrogen peroxide or 3-chloroperbenzoic acid, in a solvent such as formic acid, acetic acid, or dichloromethane, at temperatures between 0° C. and 50° C.

Alcohols 21 are produced from ketones 19 using a suitable reducing agent, e. g., sodium borohydride, in a solvent such as methanol, at temperatures between 0° C. and 50° C.

Compounds of formula (I), wherein A is N can be produced from amine precursors of general formula 22 by reaction with appropriate reagents, using methods known in the art.

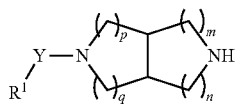

22

For instance, an amine of formula 22 is reacted with alkylating agents of general formula X—CR³R⁴—R² (15) where X is a leaving group such as Cl, Br, I, or OSO₂CH₃, leading to compounds of formula (I), wherein A is N and W is —CR³R⁴—. This reaction is performed in a solvent such as tetrahydrofuran or N,N-dimethylformamide, in the presence of a base, e. g., triethylamine or potassium carbonate, at temperatures between 0° C. and 100° C.

Alternatively, an amine of formula 22 is reacted with aldehydes or ketones of general formula R⁴—C(O)—R² (16) in a reductive amination reaction, leading to compounds of formula (I) wherein A is N, W is —CR³R⁴—, R⁴ is hydrogen, alkyl or cycloalkyl, and R³ is H. This reaction is performed in the presence of a suitable reducing agent, e. g. sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 22 is reacted with a suitable carboxylic acid of formula R²—COOH (17), leading to compounds of formula (I) wherein A is N and W is —C(O)—. The reaction is performed in the presence of a coupling agent such as 1,1'-carbonyldiimidazole, N,N'-di cyclohexylcarbodiimide, 1-(3-dimethylaminopropyl)-3-ethyl-carbodiimide hydrochloride, 0-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between –40° C. and 80° C. in the presence or absence of a base such as triethylamine, diisopropylethylamine, 4-methylmorpholine and/or 4-(dimethylamino)pyridine.

Alternatively, amine 22 is reacted with a suitable sulfonyl chloride of formula R²—SO₂Cl (18), leading to (I) wherein A is N and W is —S(O₂)—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Amines 22 can be synthesised from their tert-butyl carbamate derivatives of formula 23 by carbamate deprotection. The deprotection may be performed in the presence of a suitable acid, e. g, hydrochloric acid or trifluoroacetic acid, in a solvent such as water, 2-propanol, dichloromethane, or 1,4-dioxane, at temperatures between 0° C. and 30° C.

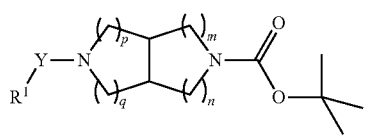

23 tert-Butyl carbamates 23 can be synthesised from amine precursors of formula 24 and appropriate reagents, using methods well known in the art.

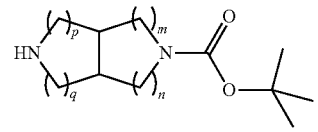

24

For instance, an amine of formula 24 is reacted with a suitable chloroformate ester of formula R¹—O—C(O)—Cl (2), or with an imidazole-1-carboxylate ester of formula (3), leading to compounds of formula 23, wherein Y is —OC (O)—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Alternatively, an amine of formula 24 is reacted with a suitable N-(chlorocarbonyl)amine of formula R¹—N(R⁵)—C(O)—Cl (4) leading to compounds of formula 23, wherein Y is —NR⁵C(O)—, or with an isocyanate of formula R¹—NCO (5) leading to compounds of formula 23, wherein Y is —NR⁵C(O)— and R⁵ is H.

Alternatively, amine 24 is reacted with a suitable carboxylic acid of formula R¹—COOH (6) leading to compounds of formula 23, wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N, N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between –40° C. and 80° C. in the presence or absence of a base such as triethylamine, diisopropylethylamine, 4-methylmorpholine and/or 4-(dimethylamino)pyridine.

Amine 24 can also be reacted with suitable acylating reagents, such as acyl chlorides of formula R¹—COCl (7) to provide compounds of formula 23, wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 24 is reacted with a suitable sulfonyl chloride, of formula R¹—SO₂Cl (8), leading to compounds of formula 23, wherein Y is —S(O₂)—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Alternatively, amine 24 is reacted with a suitable chlorooxadiazole reagent of general formula 9, or with oxadiazolone reagent 10, leading to compounds of formula 23, wherein Y is

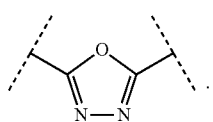

In the case where 23 is produced from amine 24 and chloro-oxadiazole 9, the reaction is performed in the presence of a base, e. g. potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where 23 is produced from amine 24 and oxadiazolone 10, the reaction is performed in the presence of a coupling agent, e. g., benzotriazol-1-yl-oxy-tris-(dimethylamino)-phosphonium hexafluorophosphate, and a base, e. g. diisopropylethylamine or 4-methylmorpholine, in a solvent such as N,N-dimethylformamide, at temperatures between 20° C. and 100° C., as described in the literature).

Alternatively, amine 24 is reacted with a suitable halothiadiazole reagent of general formula 11 (X is Cl or Br), or with thiadiazolethione reagent 12, leading to compounds of formula 23, wherein Y is

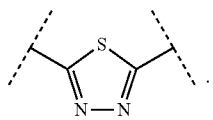

In the case where 23 is produced from amine 24 and halo-thiadiazole 11, the reaction is performed in the presence of a base, e. g. potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where 23 is produced from amine 24 and thiadiazolethione 12, the reaction is performed in a solvent such as ethanol or N,N-dimethylformamide, at temperatures between 20° C. and 100° C., as described in the literature.

Alternatively, amine 24 is acylated with a haloalkanoyl halide, e. g., bromoacetyl chloride, in the presence of a base, e. g. triethylamine, in a solvent such as dichloromethane or tetrahydrofuran, at temperatures between −78° C. and +20° C., leading to the corresponding haloalkanamide intermediate, which in the presence of a base, e. g. potassium carbonate or caesium carbonate, in a solvent such as N,N-dimethylformamide undergoes a nucleophilic substitution reaction with a substituted phenol, leading to compounds of formula 28, wherein Y is —C(O)— and $R^1$ is substituted phenoxyalkyl.

Amines of formula 24 are commercially available or can be produced as described in the literature or in the experimental section.

Also an embodiment of the present invention is a process to prepare a compound of formula (I) as defined above comprising the reaction of a compound of formula (II) in the presence of a compound of formula (III);

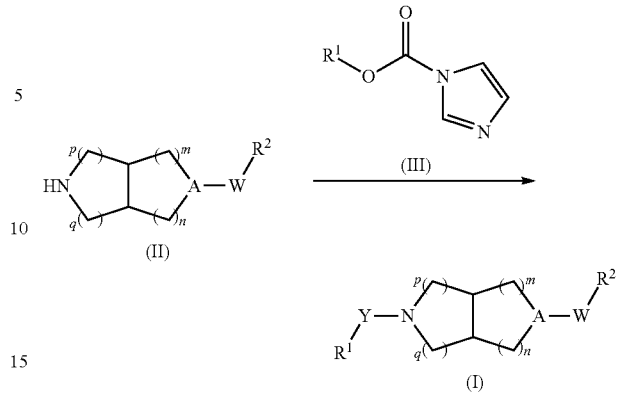

wherein $R^1$, $R^2$, A, W, m, n, p and q are as defined above, Y is —OC(O)—.

In particular, in the presence of a coupling agent such as O-(7-azabenzotriazol-1-yl)-N,N,N',N'-tetramethyluronium hexafluoro-phosphate, in a solvent such as N,N-dimethylformamide, in the presence of a base such as 4-methylmorpholine and at a temperature comprised between −78° C. and reflux, particularly between −10° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

In a particular embodiment, the compounds of formula (I) or their pharmaceutically acceptable salts and esters can be used for the treatment or prophylaxis of organ or skin fibrosis.

In another embodiment, the fibrotic disease is renal tubulo-interstitial fibrosis or glomerulosclerosis.

In another embodiment, the fibrotic disease is non-alcoholic liver steatosis, liver fibrosis or liver cirrhosis.

In another embodiment, the fibrotic disease is idiopathic pulmonary fibrosis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like.

Metabolic conditions include, but are not limited to, obesity and diabetes.

In another embodiment, the compounds of formula (I) or their pharmaceutically acceptable salts and esters can be used for the treatment or prophylaxis of cholestatic or non-cholestatic chronic pruritus.

The present invention also relates to the use of a compound according to formula (I) as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the treatment or prophylaxis of renal conditions, liver conditions and fibrotic diseases.

A particular embodiment of the present invention is a compound according to formula (I) as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula (I) as described herein for the treatment or prophylaxis of renal conditions, liver conditions and fibrotic diseases.

The present invention also relates to the use of a compound according to formula (I) as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula (I) as described herein.

Also an object of the invention is a method for the treatment or prophylaxis of renal conditions, liver conditions and fibrotic diseases, which method comprises administering an effective amount of a compound according to formula (I) as described herein.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the inflammatory condition is arthritis.

In a particular embodiment, the condition of the nervous system is neuropathic pain.

In another embodiment, the fibrotic disease is encapsulating peritonitis

In another embodiment, the fibrotic disease is idiopathic pulmonary fibrosis.

In another embodiment, the fibrotic disease is non-alcoholic liver steatosis, liver fibrosis or liver cirrhosis.

Also an embodiment of the present invention are compounds of formula (I) as described herein, when manufactured according to any one of the described processes.

Assay Procedures

Production of Human Full Length ATX, with and without His Tag

Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultrafiltration by adding Brij 35 to a final concentration of 0.02% and by adjusting the pH to 7.0 using 1 M HCl. Then the supernatant was first microfiltred through a 0.2 µm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 µM MR121 substrate in DMSO), diluted to 2-5× final concentration in assay buffer.

Test compounds (10 mM stock in DMSO, 8 µL) were obtained in 384 well sample plates (Corning Costar #3655) and diluted with 8 µL DMSO. Row-wise serial dilutions were made by transferring 8 µL cpd solution to the next row up to row O. The compound and control solutions were mixed five times and 2 µL were transferred to 384 well assay plates (Corning Costar #3702). Then, 15 µL of 41.7 nM ATX solution was added (30 nM final concentration), mixed five times and then incubated for 15 minutes at 30° C. 10 µL of MR121 substrate solution was added (1 µM final concentration), mixed 30 times and then incubated for 15 minutes at 30° C.

Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

$IC_{50}$ values for the examples of this invention are given in the table below:

| Example | IC50 (µM) |
|---------|-----------|
| 1       | 1.156     |
| 1.01    | 0.293     |
| 1.02    | 0.444     |
| 1.03    | 0.007     |
| 1.04    | 0.008     |
| 1.05    | 0.004     |
| 1.06    | 0.255     |
| 1.07    | 6.108     |
| 1.08    | 1.1995    |
| 1.09    | 0.118     |
| 1.10    | 0.002     |
| 1.11    | 0.001     |
| 1.12    | 0.44      |
| 1.13    | 0.001     |
| 1.14    | 0.064     |
| 1.15    | 0.0585    |
| 1.16    | 0.001     |
| 1.17    | 0.025     |
| 1.18    | 0.013     |
| 1.19    | 0.004     |
| 1.20    | 0.019     |

-continued

| Example | IC50 (μM) |
|---|---|
| 1.21 | 0.118 |
| 1.22 | 0.007 |
| 1.23 | 0.004 |
| 1.24 | 0.012 |
| 1.25 | 0.002 |
| 1.26 | 0.01 |
| 2 | 0.342 |
| 2.01 | 1.5 |
| 3 | 0.031 |
| 4 | 0.573 |
| 5 | 1.3445 |
| 6 | 0.6225 |
| 7 | 0.0145 |
| 7.01 | 0.001 |
| 7.02 | 0.003 |
| 7.03 | 0.004 |
| 8 | 0.0085 |
| 8.01 | 0.0075 |
| 8.02 | 0.014 |
| 8.03 | 0.0055 |
| 8.04 | 0.1665 |
| 8.05 | 0.093 |
| 8.06 | 0.003 |
| 8.07 | 0.001 |
| 8.08 | 0.0015 |
| 8.09 | 0.001 |
| 9A | 0.004 |
| 9B | 0.005 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided preferably into 1-3 individual doses, which can consist, for example, of the same amounts, should it be appropriate. It will, however, be clear that the upper limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; sat.=saturated Example 1

(3aR,6aS)-3,5-Dichlorobenzyl 5-(4-(N-methylsulfamoyl)benzoyl)hexahydropyrrolo[3,4-c]pyrrole-2(1H)-carboxylate

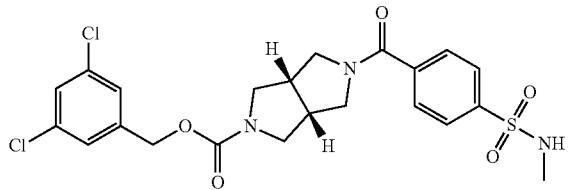 [SMILES: CNS(=O)(=O)c1ccc(C(=O)N2C[C@H]3CN(C(=O)OCc4cc(Cl)cc(Cl)c4)C[C@H]3C2)cc1]

To a solution of (3aR,6aS)-3,5-dichlorobenzyl hexahydropyrrolo[3,4-c]pyrrole-2(1H)-carboxylate hydrochloride (intermediate 1; 40 mg, 114 μmol), 4-methylmorpholine (57.5 mg, 569 μmol) and 4-(N-methylsulfamoyl)benzoic acid (24.5 mg, 114 μmol) in N,N-dimethylformamide (2 mL) was added O-(7-azabenzotriazol-1-yl)-N,N,N',N'-tetramethyluronium hexafluoro-phosphate (43.3 mg, 114 μmol) at 0° C., then the reaction mixture was allowed to reach room temperature over 16 h. After partitioning between ethyl acetate and aq. sat. sodium hydrogen carbonate solution the organic layer was washed with water and brine, dried over magnesium sulfate filtered and evaporated. Chromatography (silica gel; ethyl acetate-methanol gradient) afforded the title compound (58 mg, 99%). White foam, MS: 512.3 (M+H)$^+$.

The following examples were prepared according to example 1, replacing (3aR,6aS)-3,5-dichlorobenzyl hexahydropyrrolo[3,4-c]pyrrole-2(1H)-carboxylate hydrochloride by the appropriate amine and 4-(N-methylsulfamoyl)benzoic acid by the appropriate carboxylic acid.

| Ex. | Systematic Name | Amine/Carboxylic acid | MS, m/e |
|---|---|---|---|
| 1.01 | (3aR,6aS)-3,5-dichlorobenzyl 5-(5-hydroxypicolinoyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/5-hydroxypicolinic acid | 436.2 (M + H)+ |
| 1.02 | (3aR,6aS)-3,5-dichlorobenzyl 5-(4-hydroxybenzoyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/4-hydroxybenzoic acid | 435.2 (M + H)+ |
| 1.03 | trans-3,5-dichlorobenzyl 2-(4-sulfamoylbenzoyl)hexahydro-1H-pyrrolo[3,4-c]pyridine-5(6H)-carboxylate | (3aS,7aS)-3,5-dichlorobenzyl hexahydro-1H-pyrrolo[3,4-c]pyridine-5(6H)-carboxylate hydrochloride (intermediate 1.1)/4-sulfamoylbenzoic acid | 512.5 (M + H)+ |
| 1.04 | (3aR,6aS)-3,5-dichlorobenzyl 5-(5-sulfamoylthiophene-2-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/5-sulfamoylthiophene-2-carboxylic acid | 504.3 (M + H)+ |
| 1.05 | (3aR,6aS)-3,5-dichlorobenzyl 5-(4-sulfamoylbenzoyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/4-sulfamoylbenzoic acid | 498.3 (M + H)+ |

-continued

| Ex. | Systematic Name | Amine/Carboxylic acid | MS, m/e |
|---|---|---|---|
| 1.06 | (3aR,6aS)-3,5-dichlorobenzyl 5-(4-aminobenzoyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/4-aminobenzoic acid | 434.4 (M + H)+ |
| 1.07 | (3aR,6aS)-3,5-dichlorobenzyl 5-(5-aminopicolinoyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/5-aminopicolinic acid hydrochloride | 435.4 (M + H)+ |
| 1.08 | (3aR,6aS)-3,5-dichlorobenzyl 5-(4-cyanobenzoyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/4-cyanobenzoic acid | 444.2 (M + H)+ |
| 1.09 | (3aR,6aS)-3,5-dichlorobenzyl 5-(4-(methoxycarbonyl)benzoyl) hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1)/4-(methoxycarbonyl)-benzoic acid | 477.2 (M + H)+ |
| 1.10 | 4-{(3aS,8aR)-6-[(E)-3-(4-trifluoromethoxy-phenyl)-acryloyl]-octahydro-pyrrolo[3,4-d]azepine-2-carbonyl}-benzenesulfonamide | (E)-1-((3aR,8aS)-octahydropyrrolo[3,4-d]azepin-6(7H)-yl)-3-(4-(trifluoromethoxy)phenyl)prop-2-en-1-one hydrochloride (intermediate 2)/4-sulfamoylbenzoic acid | 538.5 (M + H)+ |

-continued

| Ex. | Systematic Name | Amine/Carboxylic acid | MS, m/e |
|---|---|---|---|
| 1.11 | (3aS,6aS)-5-(3-fluoro-4-sulfamoyl-benzoyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/3-fluoro-4-sulfamoyl-benzoic acid (CAS-RN 244606-37-9) | 532.5 (M + H)+ |
| 1.12 | (3aS,6aS)-5-(6-oxo-1,6-dihydro-pyridine-3-carbonyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/6-oxo-1,6-dihydropyridine-3-carboxylic acid | 452.5 (M + H)+ |
| 1.13 | (3aS,6aS)-5-(5-sulfamoyl-pyridine-2-carbonyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/5-sulfamoylpicolinic acid (CAS-RN 1308677-67-9) | 515.5 (M + H)+ |
| 1.14 | (3aS,6aS)-5-(1-methyl-4-sulfamoyl-1H-pyrrole-2-carbonyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/1-methyl-4-sulfamoyl-1H-pyrrole-2-carboxylic acid (CAS-RN 878218-38-3) | 517.5 (M + H)+ |
| 1.15 | (3aS,6aS)-5-(1-methyl-5-sulfamoyl-1H-pyrrole-2-carbonyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/1-methyl-5-sulfamoyl-1H-pyrrole-2-carboxylic acid (CAS-RN 306936-62-9) | 517.5 (M + H)+ |

-continued

| Ex. | Systematic Name | Amine/Carboxylic acid | MS, m/e |
|---|---|---|---|
| 1.16 | (3aS,6aS)-5-(5-sulfamoyl-pyridine-2-carbonyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/6-sulfamoylnicotinic acid (CAS-RN 285135-56-0) | 515.6 (M + H)+ |
| 1.17 | (3aS,6aS)-5-(5-hydroxy-pyridine-2-carbonyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/5-hydroxypicolinic acid | 452.4 (M + H)+ |
| 1.18 | (3aS,6aS)-5-(4-hydroxy-benzoyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/4-hydroxybenzoic acid | 451.4 (M + H)+ |
| 1.19 | (3aS,6aS)-5-(2-fluoro-4-sulfamoyl-benzoyl)-hexahydro-pyrrolo[3,4-c]pyrrole-2-carboxylic acid 4-trifluoromethoxy-benzyl ester | (3aS,6aS)-hexahydro-pyrrolo[3,4-c]pyrrole-2-carboxylic acid 4-trifluoromethoxy-benzyl ester hydrochloride (intermediate 1.2)/2-fluoro-4-sulfamoyl-benzoic acid (CAS-RN 714968-42-0) | 530.3 (M − H) |
| 1.20 | 5-{(3aR,6aR)-5-[3-(4-trifluoromethoxy-phenyl)-propionyl]-hexahydro-pyrrolo[3,4-c]pyrrole-2-carbonyl}-pyridine-2-sulfonic acid amide | 1-((3aS,6aS)-hexahydropyrrolo[3,4-c]pyrrol-2(1H)-yl)-3-(4-(trifluoromethoxy)phenyl)propan-1-one dihydrochloride (intermediate 2.2)/6-sulfamoylnicotinic acid (CAS-RN 285135-56-0) | 513.3 (M + H)+ |

-continued

| Ex. | Systematic Name | Amine/Carboxylic acid | MS, m/e |
|---|---|---|---|
| 1.21 | 5-((3aS,6aS)-5-(4-ethoxyquinoline-2-carbonyl)octahydropyrrolo[3,4-c]pyrrole-2-carbonyl)pyridine-2-sulfonamide | (4-ethoxyquinolin-2-yl)((3aS,6aS)-hexahydropyrrolo[3,4-c]pyrrol-2(1H)-yl)methanone hydrochloride (intermediate 2.1)/6-sulfamoylnicotinic acid (CAS-RN 285135-56-0) | 496.2 (M + H)+ |
| 1.22 | (3aS,6aS)-5-(3-fluoro-4-sulfamoyl-benzoyl)-hexahydro-pyrrolo[3,4-c]pyrrole-2-carboxylic acid 4-cyano-2-(2,2-dimethyl-propionylamino)-benzyl ester | (3aS,6aS)-4-cyano-2-pivalamidobenzyl hexahydropyrrolo[3,4-c]pyrrole-2(1H)-carboxylate hydrochloride (intermediate 1.3)/3-fluoro-4-sulfamoylbenzoic acid (CAS-RN 244606-37-9) | 570.3 (M − H) |
| 1.23 | (3aS,6aS)-5-(6-sulfamoyl-pyridine-3-carbonyl)-hexahydro-pyrrolo[3,4-c]pyrrole-2-carboxylic acid 4-cyano-2-(2,2-dimethyl-propionylamino)-benzyl ester | (3aS,6aS)-4-cyano-2-pivalamidobenzyl hexahydropyrrolo[3,4-c]pyrrole-2(1H)-carboxylate hydrochloride (intermediate 1.3)/6-sulfamoylnicotinic acid (CAS-RN 285135-56-0) | 553.3 (M − H) |
| 1.24 | (3aS,6aS)-5-(4-sulfamoyl-benzoyl)-hexahydro-pyrrolo[3,4-c]pyrrole-2-carboxylic acid 4-cyano-2-(2,2-dimethyl-propionylamino)-benzylester | (3aS,6aS)-4-cyano-2-pivalamidobenzyl hexahydropyrrolo[3,4-c]pyrrole-2(1H)-carboxylate hydrochloride (intermediate 1.3)/4-sulfamoylbenzoic acid | 552.3 (M − H) |

| Ex. | Systematic Name | Amine/Carboxylic acid | MS, m/e |
|---|---|---|---|
| 1.25 | (3aS,6aS)-5-(2-fluoro-4-sulfamoyl-benzoyl)-hexahydro-pyrrolo[3,4-c]pyrrole-2-carboxylic acid 4-cyano-2-(2,2-dimethyl-propionylamino)-benzyl ester | (3aS,6aS)-4-cyano-2-pivalamidobenzyl hexahydropyrrolo[3,4-c]pyrrole-2(1H)-carboxylate hydrochloride (intermediate 1.3)/2-fluoro-4-sulfamoylbenzoic acid (CAS-RN 714968-42-0) | 570.4 (M − H) |
| 1.26 | (3aS,6aS)-5-(5-sulfamoyl-pyridine-2-carbonyl)-hexahydro-pyrrolo[3,4-c]pyrrole-2-carboxylic acid 4-cyano-2-(2,2-dimethyl-propionylamino)-benzyl ester | (3aS,6aS)-4-cyano-2-pivalamidobenzyl hexahydropyrrolo[3,4-c]pyrrole-2(1H)-carboxylate hydrochloride (intermediate 1.3)/5-sulfamoylpicolinic acid (CAS-RN 1308677-67-9) | 553.3 (M − H) |

Example 2

(3aR,6aS)-3,5-Dichlorobenzyl 5-(4-acetamidobenzoyl)hexahydropyrrolo[3,4-c]pyrrole-2(1H)-carboxylate

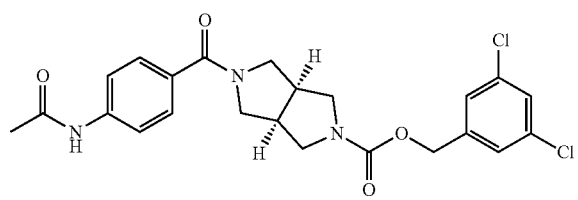 [SMILES: CC(=O)Nc1ccc(C(=O)N2C[C@H]3CN(C(=O)OCc4cc(Cl)cc(Cl)c4)C[C@H]3C2)cc1]

Acetyl chloride (8.7 mg, 110 µmol) was added at 0° C. to a suspension of (3aR,6aS)-3,5-dichlorobenzyl 5-(4-aminobenzoyl)hexahydropyrrolo[3,4-c]pyrrole-2(1H)-carboxylate (example 1.06; 40 mg, 92.1 µmol) and triethylamine (28.0 mg, 276 µmol) in dichloromethane (1 mL). The ice bath was removed, then after 90 min another portion of acetyl chloride (5.8 mg, 73 µmol) was added, then after another 2 h the reaction mixture was partitioned between dichloromethane and brine. The organic layer was dried over magnesium sulfate, filtered, and evaporated. Chromatography (silica gel; ethyl acetate-methanol gradient) produced the title compound (27 mg, 61%). White foam, MS: 476.4 (M+H)$^+$.

Example 2.1

(3aR,6aS)-3,5-Dichlorobenzyl 5-(5-acetamidopicolinoyl)hexahydropyrrolo[3,4-c]pyrrole-2(1H)-carboxylate

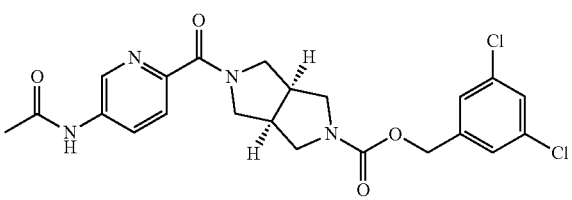 [SMILES: CC(=O)Nc1ccc(C(=O)N2C[C@H]3CN(C(=O)OCc4cc(Cl)cc(Cl)c4)C[C@H]3C2)nc1]

The title compound was produced in analogy to example 2, replacing (3aR,6aS)-3,5-dichlorobenzyl 5-(4-aminobenzoyl)hexahydropyrrolo[3,4-c]pyrrole-2(1H)-carboxylate by (3aR,6aS)-3,5-dichlorobenzyl 5-(5-aminopicolinoyl)hexahydropyrrolo[3,4-c]pyrrole-2(1H)-carboxylate (example 1.07). White solid, MS: 477.4 (M+H)$^+$.

Example 3

(3aR,6aS)-3,5-Dichlorobenzyl 5-(4-sulfamoylphenylsulfonyl)hexahydropyrrolo[3,4-c]pyrrole-2(1H)-carboxylate

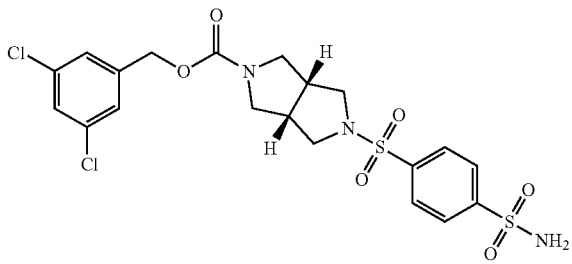 [SMILES: NS(=O)(=O)c1ccc(S(=O)(=O)N2C[C@H]3CN(C(=O)OCc4cc(Cl)cc(Cl)c4)C[C@H]3C2)cc1]

To a suspension of (3aR,6aS)-3,5-dichlorobenzyl hexahydropyrrolo[3,4-c]pyrrole-2(1H)-carboxylate hydrochloride (intermediate 1; 50 mg, 142 µmol) and pyridine (112 mg, 1.42 mmol) in tetrahydrofuran (1 mL) was added a solution of 4-sulfamoylbenzene-1-sulfonyl chloride (32.7 mg, 128 µmol) in tetrahydrofuran (1 mL) at 0° C., then the reaction mixture was stirred at room temperature for 16 h. After partitioning between ethyl acetate and sat. aq. sodium hydrogencarbonate solution, the organic layer was washed with brine, dried over magnesium sulfate, filtered, and evaporated. The residue was triturated in ethyl acetate to produce the title compound (45 mg, 59%). Light yellow solid, MS: 532.1 (M−H)⁻.

Example 4

(3aR,6aS)-3,5-Dichlorobenzyl 5-(4-(1H-tetrazol-5-yl)benzoyl)hexahydropyrrolo[3,4-c]pyrrole-2(1H)-carboxylate

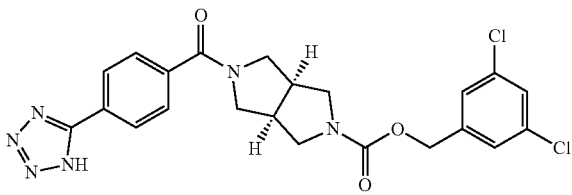 [SMILES: O=C(OCc1cc(Cl)cc(Cl)c1)N1C[C@@H]2CN(C(=O)c3ccc(-c4nnn[nH]4)cc3)C[C@@H]2C1]

To a solution of (3aR,6aS)-3,5-dichlorobenzyl 5-(4-cyanobenzoyl)hexahydropyrrolo[3,4-c]pyrrole-2(1H)-carboxylate (example 1.08; 83 mg, 187 µmol) in 2-propanol (4 mL) and water (5 mL) was added sodium azide (24.3 mg, 374 µmol) and zinc bromide (21.0 mg, 93.4 µmol). The reaction mixture was heated at 80° C. for 16 h, then another portion of sodium azide (24.3 mg, 374 µmol) and zinc bromide (21.0 mg, 93.4 µmol) was added, then after another 14 h the reaction mixture was partitioned between ethyl acetate and water. The organic layer was washed with water and brine, dried over magnesium sulfate, filtered, and evaporated. Chromatography (silica gel; gradient dichloromethane to dichloromethane/methanol 4:1) afforded the title compound (46 mg, 51%). White foam, MS: 487.4 (M+H)+.

Example 5

4-((3aR,6aS)-5-(((3,5-Dichlorobenzyloxy)carbonyl)octahydropyrrolo[3,4-c]pyrrole-2-carbonyl)benzoic acid

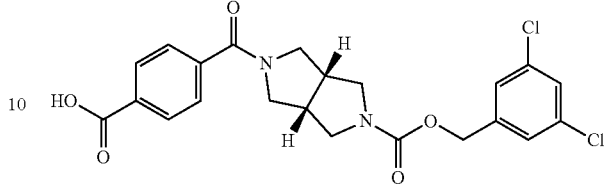

To a solution of (3aR,6aS)-3,5-dichlorobenzyl 5-(4-(methoxycarbonyl)benzoyl)hexahydro-pyrrolo[3,4-c]pyrrole-2(1H)-carboxylate (example 1.09; 82 mg, 172 µmol) in tetrahydrofuran (1.5 mL) was added 2 M aq. sodium hydroxide solution (515 µl, 1.03 mmol). The reaction mixture was stirred at room temperature for 2 h, then heated at 50° C. for 3 h, then partitioned between ethyl acetate and 1 M aq. hydrochloric acid solution. The organic layer was washed with water and brine, dried over magnesium sulfate, filtered, and evaporated to afford the title compound (74 mg, 93%). White solid, MS: 463.6 (M−H)⁻.

Example 6

(3aR,6aS)-3,5-Dichlorobenzyl 5-(5-(methylsulfonamido)picolinoyl)hexahydropyrrolo[3,4-c]pyrrole-2(1H)-carboxylate

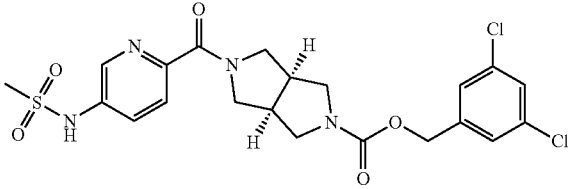 [SMILES: CS(=O)(=O)Nc1ccc(C(=O)N2C[C@H]3CN(C(=O)OCc4cc(Cl)cc(Cl)c4)C[C@H]3C2)nc1]

Step 1: (3aR,6aS)-3,5-Dichlorobenzyl 5-(5-(N-(methyl sulfonyl)methylsulfonamido)-picolinoyl)hexahydropyrrolo[3,4-c]pyrrole-2(1H)-carboxylate A solution of methanesulfonyl chloride (21 mg, 184 µmol) in dichloromethane (0.5 mL) was added dropwise at 0° C. to a solution of (3aR,6aS)-3,5-dichlorobenzyl 5-(5-aminopicolinoyl)-hexahydropyrrolo[3,4-c]pyrrole-2(1H)-carboxylate (example 1.07; 40 mg, 91.9 µmol) and triethylamine (27.9 mg, 276 µmol) in dichloromethane (1 mL). The ice bath was removed, then after 18 h the reaction mixture was partitioned between dichloromethane and water. The organic layer was washed with brine, dried over magnesium sulfate, filtered, and evaporated. Chromatography (silica gel; gradient dichloromethane to dichloromethane/methanol/25% aq. ammonia solution 95:5:0.25) produced the title compound (42 mg, 77%). White foam, MS: 591.4 (M+H)⁺.

Step 2: (3aR,6aS)-3,5-Dichlorobenzyl 5-(5-(methylsulfonamido)picolinoyl)hexahydro-pyrrolo[3,4-c]pyrrole-2(1H)-carboxylate To a solution of (3aR,6aS)-3,5-dichlorobenzyl 5-(5-(N-(methylsulfonyl)methylsulfonamido)-picolinoyl)hexahydropyrrolo[3,4-c]pyrrole-2(1H)-carboxylate (36 mg, 60.9 µmol) in tetrahydrofuran (0.5 mL) was added 1 M aq.

sodium hydroxide solution (122 µl, 122 µmol), then after 1 h the reaction mixture was partitioned between ethyl acetate and sat. aq. ammonium chloride solution. The organic layer was washed with water and brine, dried over magnesium sulfate, filtered, and evaporated to afford the title compound (29 mg, 93%). White foam, MS: 513.4 (M+H)$^+$.

Example 7

(3aS,6aS)-5-(4-Sulfamoyl-benzoyl)-hexahydro-pyrrolo[3,4-c]pyrrole-2-carboxylic acid 3-chloro-5-methanesulfonyl-benzyl ester

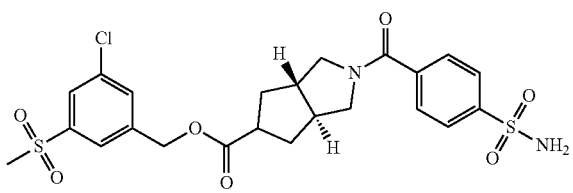 [SMILES: CS(=O)(=O)c1cc(Cl)cc(COC(=O)C2C[C@@H]3CN(C(=O)c4ccc(S(N)(=O)=O)cc4)C[C@H]3C2)c1]

To a solution of (3-chloro-5-(methyl sulfonyl)phenyl)methanol (intermediate 5; 23.3 mg, 105 µmol) in acetonitrile (4 ml) was added N,N'-carbonyldiimidazole (18.0 mg, 111 µmol) at room temperature, then after 2 h triethylamine (53.4 mg, 527 µmol) and 4-((3aR,6aR)-octahydropyrrolo[3,4-c]pyrrole-2-carbonyl)benzenesulfonamide hydrochloride (intermediate 4; 35 mg, 105 µmol) were added and the reaction mixture was heated at reflux for 15 h. After cooling the reaction mixture was partitioned between ethyl acetate and sat. aq. ammonium chloride solution. The aqueous layer was back-extracted with ethyl acetate, then the combined organic layers were washed with brine, dried over magnesium sulfate, filtered, and evaporated. The residue was triturated in tert-butyl methyl ether to afford the title compound (26 mg, 46%). White solid, MS: 542.5 (M+H)$^+$.

The following examples were prepared according to example 7, replacing 4-((3aR,6aR)-octahydropyrrolo[3,4-c]pyrrole-2-carbonyl)benzenesulfonamide hydrochloride by the appropriate amine and (3-chloro-5-(methylsulfonyl)phenyl)methanol by the appropriate alcohol.

| Ex. | Systematic Name | Amine/Alcohol | MS, m/e |
| --- | --- | --- | --- |
| 7.01 | (3aR,6aS)-5-(4-sulfamoyl-benzoyl)-hexahydro-pyrrolo[3,4-c]pyrrole-2-carboxylic acid 2-fluoro-4-trifluoromethoxy-benzyl ester | 4-((3aR,6aS)-octahydropyrrolo[3,4-c]pyrrole-2-carbonyl)-benzenesulfonamide hydrochloride (intermediate 4.1)/(2-fluoro-4-(trifluoromethoxy)-phenyl)methanol | 532.5 (M + H)$^+$ |
| 7.02 | (3aR,6aS)-5-(4-sulfamoyl-benzoyl)-hexahydro-pyrrolo[3,4-c]pyrrole-2-carboxylic acid 4-trifluoromethoxy-benzyl ester | 4-((3aR,6aS)-octahydropyrrolo[3,4-c]pyrrole-2-carbonyl)-benzenesulfonamide hydrochloride (intermediate 4.1)/(4-(trifluoromethoxy)-phenyl)methanol | 514.6 (M + H)$^+$ |
| 7.03 | (3aR,6aS)-5-(4-sulfamoyl-benzoyl)-hexahydro-pyrrolo[3,4-c]pyrrole-2-carboxylic acid 4-trifluoromethoxy-benzyl ester | 4-((3aR,6aR)-octahydropyrrolo[3,4-c]pyrrole-2-carbonyl)-benzenesulfonamide hydrochloride (intermediate 4)/(4-(trifluoromethoxy)-phenyl)methanol | 514.5 (M + H)$^+$ |

Example 8

4-{(3aR,6aR)-5-[3-(4-Trifluoromethoxy-phenyl)-propionyl]-hexahydro-pyrrolo[3,4-c]pyrrole-2-carbonyl}-benzenesulfonamide

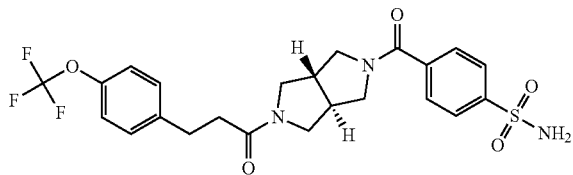 [SMILES: NS(=O)(=O)c1ccc(C(=O)N2C[C@H]3CN(C(=O)CCc4ccc(OC(F)(F)F)cc4)C[C@@H]3C2)cc1]

To a white suspension of 4-((3aR,6aR)-octahydropyrrolo[3,4-c]pyrrole-2-carbonyl)benzenesulfonamide hydrochloride (intermediate 4; 40 mg, 121 µmol), N-methylmorpholine (61.0 mg, 603 µmol) and 3-(4-(trifluoromethoxy)phenyl)propanoic acid (28.2 mg, 121 µmol) in N,N-dimethylformamide (5 ml) was added O-(7-azabenzotriazol-1-yl)-N,N,N',N'-tetramethyluronium hexafluoro-phosphate (45.8 mg, 121 µmol) at 0° C., and the ice bath was removed after 15 min. After 16 h, the reaction mixture was partitioned between dichloromethane and sat. aq. sodium hydrogencarbonate solution. The organic layer was washed with sat. aq. ammonium chloride solution and brine, dried over magnesium sulfate, filtered and evaporated. After trituration in tert-butyl methyl ether the precipitate was collected by filtration to afford the title compound (44 mg, 71%). White solid, MS: 512.5 (M+H)$^+$.

The following examples were produced in analogy to example 8, replacing 4-((3aR,6aR)-octahydropyrrolo[3,4-c]pyrrole-2-carbonyl)benzenesulfonamide hydrochloride by the appropriate amine and 3-(4-(trifluoromethoxy)phenyl)propanoic acid by the appropriate carboxylic acid.

| Ex. | Systematic Name | Amine/ Carboxylic acid | MS, m/e |
|---|---|---|---|
| 8.01 | 4-{(3aR,6aR)-5-[(E)-3-(4-trifluoromethoxy-phenyl)-acryloyl]-hexahydro-pyrrolo[3,4-c]pyrrole-2-carbonyl}-benzenesulfonamide | 4-((3aR,6aR)-octahydropyrrolo[3,4-c]pyrrole-2-carbonyl)-benzenesulfonamide hydrochloride (intermediate 4)/(E)-3-(4-(trifluoromethoxy)-phenyl)acrylic acid | 510.5 (M + H)$^+$ |
| 8.02 | 4-[(3aR,6aS)-5-(4-isopropoxy-naphthalene-2-carbonyl)-hexahydro-pyrrolo[3,4-c]pyrrole-2-carbonyl]-benzenesulfonamide | 4-((3aR,6aS)-octahydropyrrolo[3,4-c]pyrrole-2-carbonyl)-benzenesulfonamide hydrochloride (intermediate 4.1)/4-isopropoxy-2-naphthoic acid (CAS-RN 1368865-02-4) | 508.4 (M + H)$^+$ |
| 8.03 | 4-{(3aR,6aS)-5-[1-(2,2,2-trifluoro-ethoxy)-isoquinoline-3-carbonyl]-hexahydro-pyrrolo[3,4-c]pyrrole-2-carbonyl}-benzenesulfonamide | 4-((3aR,6aS)-octahydropyrrolo[3,4-c]pyrrole-2-carbonyl)-benzenesulfonamide hydrochloride (intermediate 4.1)/1-(2,2,2-trifluoroethoxy)-isoquinoline-3-carboxylic acid (CAS-RN 1096982-79-4) | 549.6 (M + H)$^+$ |

| Ex. | Systematic Name | Amine/ Carboxylic acid | MS, m/e |
|---|---|---|---|
| 8.04 | 4-[(3aR,6aS)-5-(1-Methyl-5-trifluoromethoxy-1H-indole-2-carbonyl)-hexahydro-pyrrolo[3,4-c]pyrrole-2-carbonyl]-benzenesulfonamide | 4-((3aR,6aS)-octahydropyrrolo[3,4-c]pyrrole-2-carbonyl)-benzenesulfonamide hydrochloride (intermediate 4.1)/1-methyl-5-(trifluoro-methoxy)-1H-indole-2-carboxylic acid (CAS-RN 1257122-42-1) | 537.5 (M + H)+ |
| 8.05 | 4-[(3aR,6aS)-5-(4-Isopropoxy-quinoline-2-carbonyl)-hexahydro-pyrrolo[3,4-c]pyrrole-2-carbonyl]-benzenesulfonamide | 4-((3aR,6aS)-octahydropyrrolo[3,4-c]pyrrole-2-carbonyl)-benzenesulfonamide hydrochloride (intermediate 4.1)/4-isopropoxyquinoline-2-carboxylic acid (CAS-RN 1406553-19-2) | 509.6 (M + H)+ |
| 8.06 | 4-[(3aS,6aR)-5-(4'-chloro-biphenyl-4-carbonyl)-hexahydro-pyrrolo[3,4-c]pyrrole-2-carbonyl]-benzenesulfonamide | 4-((3aR,6aS)-octahydropyrrolo[3,4-c]pyrrole-2-carbonyl)-benzenesulfonamide hydrochloride (intermediate 4.1)/4'-chlorobiphenyl-4-carboxylic acid (CAS-RN 5748-41-4) | 510.5 (M + H)+ |
| 8.07 | 4-{(3aS,6aR)-5-[3-(2-fluoro-4-trifluoromethoxy-phenyl)-propionyl]-hexahydro-pyrrolo[3,4-c]pyrrole-2-carbonyl}-benzenesulfonamide | 4-((3aR,6aS)-octahydropyrrolo[3,4-c]pyrrole-2-carbonyl)-benzenesulfonamide hydrochloride (intermediate 4.1)/3-(2-fluoro-4-(trifluoro-methoxy)phenyl)-propanoic acid (CAS-RN 1240257-16-2) | 530.3 (M + H)+ |

-continued

| Ex. | Systematic Name | Amine/ Carboxylic acid | MS, m/e |
|---|---|---|---|
| 8.08 | 4-{(3aS,6aR)-5-[3-(4-trifluoromethoxy-phenyl)-propionyl]-hexahydro-pyrrolo[3,4-c]pyrrole-2-carbonyl}-benzenesulfonamide | 4-((3aR,6aS)-octahydropyrrolo[3,4-c]pyrrole-2-carbonyl)-benzenesulfonamide hydrochloride (intermediate 4.1)/3-(4-(trifluoromethoxy)-phenyl)propanoic acid | 512.3 (M + H)+ |
| 8.09 | 4-((3aR,6aR)-5-(3-(2-fluoro-4-(trifluoromethoxy)phenyl)propanoyl)octahydropyrrolo[3,4-c]pyrrole-2-carbonyl)benzenesulfonamide | 4-((3aR,6aR)-octahydropyrrolo[3,4-c]pyrrole-2-carbonyl)-benzenesulfonamide hydrochloride (intermediate 4)/3-(2-fluoro-4-(trifluoromethoxy)phenyl)-propanoic acid (CAS-RN 1240257-16-2) | 530.5 (M + H)+ |

Examples 9A and 9B (−)-trans-3,5-Dichlorobenzyl 2-(4-sulfamoylbenzoyl)hexahydro-1H-pyrrolo[3,4-c]pyridine-5(6H)-carboxylate and (+)-trans-3,5-dichlorobenzyl 2-(4-sulfamoylbenzoyl)hexahydro-1H-pyrrolo[3,4-c]pyridine-5(6H)-carboxylate

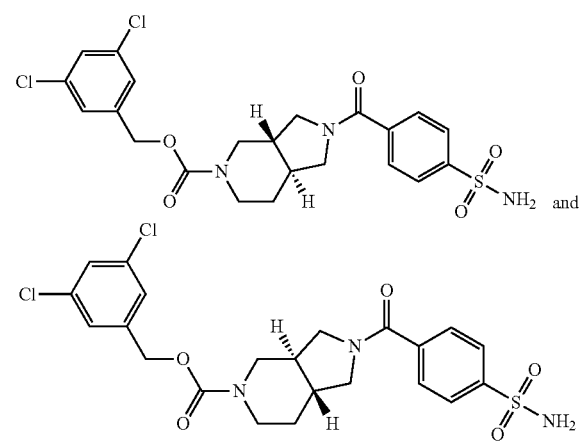

The racemate, trans-3,5-dichlorobenzyl 2-(4-sulfamoylbenzoyl)hexahydro-1H-pyrrolo[3,4-c]pyridine-5(6H)-carboxylate (example 1.03; 60 mg, 117 μmol) was separated by preparative HPLC using a Reprosil Chiral-NR column as the stationary phase and heptane/ethanol 3:2 as the mobile phase. This produced the faster eluting (−)-enantiomer (example 9A; 23 mg, 38%; white solid, MS: 512.4 (M+H)+), and the slower eluting (+)-enantiomer (example 9B; 22 mg, 36%; orange foam, MS: 512.4 (M+H)+).

INTERMEDIATES

Intermediate 1

(3aR,6aS)-3,5-Dichlorobenzyl hexahydropyrrolo[3,4-c]pyrrole-2(1H)-carboxylate hydrochloride Step 1: (3aR,6aS)-2-tert-Butyl 5-(3,5-dichlorobenzyl) tetrahydropyrrolo[3,4-c]pyrrole-2,5(1H,3H)-dicarboxylate To a light brown solution of (3,5-dichlorophenyl)methanol (425 mg, 2.35 mmol) in dichloromethane (7 mL) was added N,N'-carbonyldiimidazole (401 mg, 2.47 mmol). The solution was stirred at room temperature for 3 h, then (3aR,6aS)-tert-butyl hexahydropyrrolo[3,4-c]pyrrole-2(1H)-carboxylate (CAS-RN 250275-15-1; 526 mg, 2.35 mmol) was added, then after 15 h the reaction mixture was partitioned between 1 M aq. hydrochloric acid solution and dichloromethane. The organic layer was washed with brine, dried over magnesium sulfate, filtered and evaporated to afford the title compound (972 mg, 99%). Light brown viscous oil, MS: 359.2 (M-C(CH₃)₃+H)+.

Step 2: (3aR,6aS)-3,5-Dichlorobenzyl hexahydropyrrolo[3,4-c]pyrrole-2(1H)-carboxylate hydrochloride To a solution of (3aR,6aS)-2-tert-butyl 5-(3,5-dichlorobenzyl) tetrahydropyrrolo[3,4-c]pyrrole-2,5(1H,3H)-dicarboxylate (962 mg, 2.32 mmol) in 2-propanol (4 mL) was added hydrochloric acid (5-6 M in 2-propanol) (11.6 mL, 57.9 mmol), then after 3 h the reaction mixture was evaporated. The residue taken up in ethyl acetate and a few drops of ethanol, then the precipitate was collected by filtration to produce the title compound (738 mg, 91%). White solid, MS: 315.3 (M+H)+.

The following intermediates were prepared according to intermediate 1, replacing (3aR,6aS)-tert-butyl hexahydropyrrolo[3,4-c]pyrrole-2(1H)-carboxylate by the appropriate amine and (3,5-dichlorophenyl)methanol by the appropriate alcohol.

| No. | Systematic Name | Amine | Alcohol | MS, m/e |
|---|---|---|---|---|
| 1.1 | trans-3,5-dichlorobenzyl hexahydro-1H-pyrrolo[3,4-c]pyridine-5(6H)-carboxylate hydrochloride | trans-tert-butyl hexahydro-1H-pyrrolo[3,4-c]pyridine-2(3H)-carboxylate (CAS-RN 1251014-37-5) | (3,5-dichlorophenyl)-methanol | 329.4 $(M + H)^+$ |
| 1.2 | (3aS,6aS)-hexahydro-pyrrolo[3,4-c]pyrrole-2-carboxylic acid 4-trifluoromethoxy-benzyl ester hydrochloride | (3aR,6aR)-tert-butyl hexahydropyrrolo[3,4-c]pyrrole-2(1H)-carboxylate (intermediate 3.1) | (4-(trifluoro-methoxy)-phenyl)-methanol | 331.5 $(M + H)^+$ |

Intermediate 2

(E)-1-((3aR,8aS)-Octahydropyrrolo[3,4-d]azepin-6(7H)-yl)-3-(4-(trifluoromethoxy)-phenyl)prop-2-en-1-one hydrochloride Step 1: (3aR,8aS)-tert-butyl 6-((E)-3-(4-(trifluoromethoxy)phenyl)acryloyl)octahydro-pyrrolo[3,4-d]azepine-2(1H)-carboxylate To a solution of (3aR,8aS)-tert-butyl octahydropyrrolo[3,4-d]azepine-2(1H)-carboxylate hydrochloride (CAS-RN 1251013-07-6; 1.5 g, 5.42 mmol), 4-methylmorpholine (2.19 g, 21.7 mmol) and (E)-3-(4-(trifluoromethoxy)phenyl) acrylic acid (1.26 g, 5.42 mmol) in N,N-dimethylformamide (30 ml) was added O-(7-azabenzotriazol-1-yl)-N,N,N',N'-tetramethyluronium hexafluoro-phosphate (2.06 g, 5.42 mmol) at 0° C. After 60 min the ice bath was removed, then after 16 h the reaction mixture was partitioned between ethyl acetate and sat. aq. sodium hydrogencarbonate solution. The organic layer was washed with sat. aq. ammonium chloride solution, water, and brine, dried over magnesium sulfate, filtered, and evaporated. The residue was triturated in heptane/ethyl acetate 9:1 to produce the title compound (2.20 g, 89%). White solid, MS: 399.5 (M-isobutene+H)$^+$.

Step 2: (E)-1-((3aR,8aS)-Octahydropyrrolo[3,4-d]azepin-6(7H)-yl)-3-(4-(trifluoromethoxy)-phenyl)prop-2-en-1-one hydrochloride The title compound was produced in analogy to intermediate 1, step 2 from (3aR,8aS)-tert-butyl 6-((E)-3-(4-(trifluoromethoxy)phenyl)acryloyl)octahydropyrrolo[3,4-d]azepine-2(1H)-carboxylate. White solid, MS: 355.5 (M+H)$^+$.

The following intermediates were prepared according to intermediate 2, replacing (3aR,8aS)-tert-butyl octahydropyrrolo[3,4-d]azepine-2(1H)-carboxylate hydrochloride by the appropriate amine and (E)-3-(4-(trifluoromethoxy)phenyl) acrylic acid by the appropriate carboxylic acid.

Intermediate 3

(3aS,6aS)-tert-Butyl hexahydropyrrolo[3,4-c]pyrrole-2(1H)-carboxylate

Step 1: (3R,4R)-tert-Butyl 3,4-bis((methylsulfonyloxy)methyl)pyrrolidine-1-carboxylate To a solution of (3R,4R)-tert-butyl 3,4-bis(hydroxymethyl)pyrrolidine-1-carboxylate (CAS-RN 895245-32-6; 2.97 g, 12.8 mmol) and N,N-diisopropylethylamine (9.96 g, 77.0 mmol) in dichloromethane (70 ml) was added a solution of methanesulfonyl chloride (4.41 g, 38.5 mmol) in dichloromethane (5 ml) dropwise at 0° C., then after 1 h the reaction mixture was treated with sat. aq. ammonium chloride and extracted with ethyl acetate. The organic layer was washed with sat. aq. sodium hydrogencarbonate solution and brine, dried over magnesium sulfate, filtered, and evaporated. Chromatography (silica gel; heptane-ethyl acetate gradient) produced the title compound (4.22 g, 85%). Light yellow oil, MS: 332.4 (M-isobutene+H)$^+$.

Step 2: (3aS,6aS)-tert-Butyl 5-benzylhexahydropyrrolo[3,4-c]pyrrole-2(1H)-carboxylate To a solution of (3R,4R)-tert-butyl 3,4-bis((methylsulfonyloxy)methyl)pyrrolidine-1-carboxylate (4.22 g, 10.9 mmol) in acetonitrile (100 ml) was added potassium carbonate (15.1 g, 109 mmol) and phenylmethanamine (3.5 g, 32.7 mmol). The reaction mixture was heated at 95° C. for 45 h, then cooled to room temperature and partitioned between ethyl acetate and water. The organic layer was washed with sat. aq. ammonium chloride solution, sat. aq. sodium hydrogencarbonate solution, and brine, dried over magnesium sulfate, filtered, and evaporated. Chromatography (silica gel; ethyl acetate-methanol gradient) produced the title compound (2.23 g 68%). Light yellow solid, MS: 303.5 (M+H)$^+$.

| No. | Systematic Name | Amine | Carboxylic acid | MS, m/e |
|---|---|---|---|---|
| 2.1 | (4-ethoxyquinolin-2-yl)((3aS,6aS)-hexa-hydropyrrolo[3,4-c]pyrrol-2(1H)-yl)methanone hydrochloride | (3aR,6aR)-tert-butyl hexahydropyrrolo[3,4-c]pyrrole-2(1H)-carboxylate (intermediate 3.1) | 4-ethoxy-quinoline-2-carboxylic acid (CAS-RN 40609-78-7) | 312.2 $(M + H)^+$ |
| 2.2 | 1-((3aS,6aS)-hexahydro-pyrrolo[3,4-c]pyrrol-2(1H)-yl)-3-(4-(trifluoro-methoxy)phenyl)propan-1-one dihydrochloride | (3aR,6aR)-tert-butyl hexahydropyrrolo[3,4-c]pyrrole-2(1H)-carboxylate (intermediate 3.1) | 3-(4-(trifluoro-methoxy)-phenyl)-propanoic acid | 329.5 $(M + H)^+$ |

Step 3: (3aS,6aS)-tert-Butyl hexahydropyrrolo[3,4-c]pyrrole-2(1H)-carboxylate To a solution of (3aS,6aS)-tert-butyl 5-benzylhexahydropyrrolo[3,4-c]pyrrole-2(1H)-carboxylate (2.22 g, 7.34 mmol, Eq: 1.00) in methanol (20 mL) was added palladium (10% on carbon, 220 mg, 7.34 mmol), and the reaction mixture was stirred under a hydrogen atmosphere (1 bar) at room temperature for 24 h, then insoluble material was removed by filtration through diatomaceous earth. The filtrate was concentrated to produce the title compound (1.60 g, 100%). White waxy solid, MS: 213.5 (M+H)$^+$.

Intermediate 3.1

(3aR,6aR)-tert-Butyl hexahydropyrrolo[3,4-c]pyrrole-2(1H)-carboxylate

The title compound was produced in analogy to intermediate 3, replacing (3R,4R)-tert-butyl 3,4-bis(hydroxymethyl)pyrrolidine-1-carboxylate by (3S,4S)-tert-butyl 3,4-bis(hydroxymethyl)pyrrolidine-1-carboxylate (CAS-RN 895245-30-4). White waxy solid, MS: 213.3 (M+H)$^+$.

Intermediate 4

4-((3aR,6aR)-Octahydropyrrolo[3,4-c]pyrrole-2-carbonyl)benzenesulfonamide hydrochloride

Step 1: (3aS,6aS)-tert-Butyl 5-(4-sulfamoylbenzoyl) hexahydropyrrolo[3,4-c]pyrrole-2(1H)-carboxylate To a solution of (3aS,6aS)-tert-butyl hexahydropyrrolo[3,4-c]pyrrole-2(1H)-carboxylate (intermediate 3; 206 mg, 970 µmol), N-methylmorpholine (294 mg, 2.91 mmol) and 4-sulfamoylbenzoic acid (203 mg, 970 µmol) in N,N-dimethylformamide (10 ml) was added O-(7-azabenzotriazol-1-yl)-N,N,N',N'-tetramethyluronium hexafluoro-phosphate (369 mg, 970 µmol) at 0° C., then after 10 min the ice-bath was removed. After 16 h the reaction mixture was partitioned between dichloromethane and sat. aq. sodium hydrogencarbonate solution. The organic layer was washed with sat. aq. ammonium chloride solution and brine, dried over magnesium sulfate, filtered and evaporated. After trituration in tert-butyl methyl ether the precipitate was collected by filtration to afford the title compound (348 mg, 91%). Light yellow solid, MS: 396.6 (M+H)$^+$.

Step 2: 4-((3aR,6aR)-Octahydropyrrolo[3,4-c]pyrrole-2-carbonyl)benzenesulfonamide hydrochloride (intermediate 4)

The title compound was produced in analogy to intermediate 1, step 2 from (3aS,6aS)-tert-butyl 5-(4-sulfamoylbenzoyl)hexahydropyrrolo[3,4-c]pyrrole-2(1H)-carboxylate. Light yellow solid, MS: 296.5 (M+H)$^+$.

Intermediate 5

(3-Chloro-5-(methylsulfonyl)phenyl)methanol

To a solution of 3-chloro-5-(methylsulfonyl)benzoic acid (CAS-RN 151104-63-1; 500 mg, 2.13 mmol) in tetrahydrofuran (5 mL) was added slowly borane-tetrahydrofuran complex solution (1 M solution in tetrahydrofuran, 5.33 mL, 5.33 mmol) at 0° C., then after 3 h the ice-bath was removed and the reaction mixture was stirred at room temperature overnight. The reaction mixture was then carefully treated with methanol (3 mL) and evaporated. The residue was partitioned between ethyl acetate and water. The organic layer was washed with brine, dried over magnesium sulfate, filtered, and evaporated. Chromatography (silica gel; heptane-ethyl acetate gradient afforded the title compound (428 mg, 91%). White solid, MS: 221.3 (M+H)$^+$.

Intermediate 6

N-(5-Cyano-2-(hydroxymethyl)phenyl)pivalamide

Step 1: Methyl 4-cyano-2-pivalamidobenzoate

To a solution of methyl 2-amino-4-cyanobenzoate (CAS-RN 159847-83-3; 776 mg, 4.4 mmol) in pyridine (6 mL) was added pivaloyl chloride (637 mg, 5.29 mmol) dropwise at 0° C., then after 2 h the reaction mixture was partitioned between 1 M aq. hydrochloric acid solution and ethyl acetate/2-methyltetrahydrofuran. The organic layer was washed with water, 2 M aq. sodium carbonate solution, and brine, dried over magnesium sulfate, filtered, and evaporated. The residue was triturated in ethyl acetate to afford the title compound (819 mg). The mother liquor was evaporated and triturated in tert-butyl methyl ether to produce a second crop of product (148 mg). Combined yield: 967 mg (84%). White solid, MS: 261.1 (M−H)$^-$.

N-(5-cyano-2-(hydroxymethyl)phenyl)pivalamide

A suspension of calcium chloride (592 mg, 5.33 mmol) in ethanol (15 mL) was added at room temperature to a solution of methyl 4-cyano-2-pivalamidobenzoate (694 mg, 2.67 mmol) in tetrahydrofuran (15 mL), then sodium borohydride (403 mg, 10.7 mmol) was added. After 2 h the reaction mixture was poured upon ice water and sat. ammonium chloride solution and extracted with ethyl acetate. The organic layer was washed with brine, dried over magnesium sulfate, filtered, and evaporated. The residue was triturated in tert-butyl methyl ether to produce the title compound (293 mg). The mother liquor was evaporated and purified by chromatography (dichloromethane-methanol gradient) to produce another crop of product (240 mg). Combined yield: 533 mg; (86%). White solid, MS: 231.1 (M−H)$^-$.

The invention claimed is:
1. A compound of formula (I):

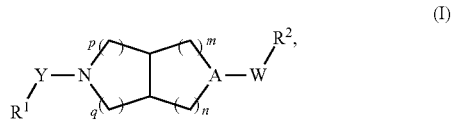

wherein:
R$^1$ is substituted cycloalkyl, substituted cycloalkylalkyl, substituted phenyl, substituted phenylalkyl, substituted phenoxyalkyl, substituted phenylcycloalkyl, substituted phenylalkenyl, substituted phenylalkynyl, substituted naphthyl, substituted naphthylalkyl, substituted naphthyloxyalkyl, substituted naphthylalkenyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted indolyl, substituted quinolyl, substituted isoquinolyl, substituted 2,3-dihydro-1H-isoindol-2-yl, substituted 1H-indol-2-yl, or substituted benzofuran-2-yl,
  wherein substituted cycloalkyl, substituted cycloalkylalkyl, substituted phenyl, substituted phenylalkyl, substituted phenoxyalkyl, substituted phenylcycloalkyl, substituted phenylalkenyl, substituted phenylalkynyl, substituted naphthyl, substituted naphthylalkyl, substituted naphthyloxyalkyl, substituted naphthylalkenyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted indolyl, substituted quinolyl, substituted isoquinolyl, substituted 2,3-dihydro-1H-isoindol-2-yl, substituted 1H-indol-2-yl, and substituted benzofuran-2-yl are substituted with $R^7$, $R^8$ and $R^9$;

$R^2$ is substituted phenyl, substituted pyridinyl, substituted pyrrolyl, oxodihydropyridinyl, or substituted thiophenyl, wherein substituted phenyl, substituted pyridinyl, substituted pyrrolyl, and substituted thiophenyl are substituted with $R^{10}$, $R^{11}$ and $R^{12}$;

Y is —OC(O)—, —NR$^5$C(O)—, —C(O)—, —S(O)$_2$—,

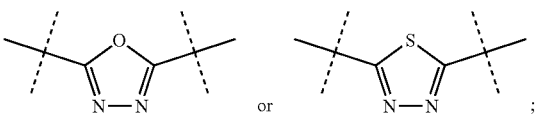

or

A is —N—;
W is —O—, —S—, —NR$^6$—, —C(O)—, —S(O)$_2$—, or —CR$^3$R$^4$—;
$R^3$ and $R^4$ are independently selected from H, halogen, alkyl and cycloalkyl;
$R^5$ and $R^6$ are independently selected from H, alkyl and cycloalkyl;
$R^7$, $R^8$ and $R^9$ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, halogen, hydroxy, cyano, alkylsulfanyl, haloalkylsulfanyl, cycloalkylsulfanyl, alkylsulfinyl, haloalkylsulfinyl, cycloalkylsulfinyl, alkylsulfonyl, haloalkylsulfonyl, cycloalkylsulfonyl, substituted aminosulfonyl, substituted amino, and substituted aminoalkyl,
  wherein substituted aminosulfonyl, substituted amino, and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl, and cycloalkylcarbonyl, and
  wherein substituted phenyl and substituted pyridinyl are optionally substituted with one to three substituents independently selected from alkyl, halogen, haloalkyl, alkoxy, and haloalkoxy,
  wherein at least one of $R^7$, $R^8$ and $R^9$ is not H;
$R^{10}$ is substituted aminosulfonyl, alkoxycarbonyl, alkylcarbonylamino, alkylsulfonylamino, substituted amino, carboxy, cyano, hydroxyl, or tetrazolyl,
  wherein substituted amino is substituted on the nitrogen atom with one to two substituents independently selected from H, alkyl, cycloalkyl, cycloalkylalkyl, hydroxyalkyl and alkoxyalkyl;
$R^{11}$ and $R^{12}$ are independently selected from H, alkyl, cycloalkyl, alkoxy, halogen and haloalkyl; and
m, n, p and q are independently selected from 1 or 2;
or a pharmaceutically acceptable salt thereof.

2. The compound according to claim 1, or a pharmaceutically acceptable salt thereof, wherein $R^1$ is substituted phenyl, substituted phenylalkyl, substituted phenylalkenyl, substituted naphthyl, substituted indolyl, substituted quinolyl, or substituted isoquinolyl, wherein substituted phenyl, substituted phenylalkyl, substituted phenylalkenyl, substituted naphthyl, substituted indolyl, substituted quinolyl and substituted isoquinolyl are substituted with $R^7$, $R^8$, and $R^9$.

3. The compound according to claim 1, or a pharmaceutically acceptable salt thereof, wherein $R^1$ is phenylalkyl substituted with $R^7$, $R^8$, and $R^9$.

4. The compound according to claim 3, or a pharmaceutically acceptable salt thereof, wherein $R^1$ is 3,5-dichlorobenzyl, 4-trifluoromethoxybenzyl, or 4-trifluoromethoxyphenylethyl.

5. The compound according to claim 1, or a pharmaceutically acceptable salt thereof, wherein $R^2$ is substituted phenyl or substituted pyridinyl, wherein substituted phenyl and substituted pyridinyl are substituted with $R^{10}$, $R^{11}$, and $R^{12}$.

6. The compound according to claim 5, or a pharmaceutically acceptable salt thereof, wherein $R^2$ is phenyl substituted with $R^{10}$, $R^{11}$, and $R^{12}$.

7. The compound according to claim 5, or a pharmaceutically acceptable salt thereof, wherein $R^2$ is 4-aminosulfonylphenyl, 3-fluoro-4-aminosulfonylphenyl, 3-aminosulfonylpyridin-6-yl, or 2-aminosulfonylpyridin-5-yl.

8. The compound according to claim 1, or a pharmaceutically acceptable salt thereof, wherein Y is —OC(O)— or —C(O)—.

9. The compound according to claim 1, or a pharmaceutically acceptable salt thereof, wherein W is —C(O)— or —S(O)$_2$—.

10. The compound according to claim 9, or a pharmaceutically acceptable salt thereof, wherein W is —C(O)—.

11. The compound according to claim 1, or a pharmaceutically acceptable salt thereof, wherein $R^7$, $R^8$ and $R^9$ are independently selected from H, alkoxy, haloalkoxy, halogen, alkylsulfonyl, and phenyl substituted with one halogen, and wherein at least one of $R^7$, $R^8$, and $R^9$ is not H.

12. The compound according to claim 1, or a pharmaceutically acceptable salt thereof, wherein $R^7$ is alkoxy, haloalkoxy, halogen, or phenyl substituted with one halogen.

13. The compound according to claim 12, or a pharmaceutically acceptable salt thereof, wherein $R^7$ is haloalkoxy or halogen.

14. The compound according to claim 1, or a pharmaceutically acceptable salt thereof, wherein $R^8$ is H, halogen, or alkylsulfonyl.

15. The compound according to claim 14, or a pharmaceutically acceptable salt thereof, wherein $R^8$ is H or halogen.

16. The compound according to claim 1, or a pharmaceutically acceptable salt thereof, wherein $R^9$ is H.

17. The compound according to claim 1, or a pharmaceutically acceptable salt thereof, wherein $R^{10}$ is aminosulfonyl.

18. The compound according to claim 1, or a pharmaceutically acceptable salt thereof, wherein $R^{11}$ and $R^{12}$ are independently selected from H, alkyl, and halogen.

19. The compound according to claim 1, or a pharmaceutically acceptable salt thereof, wherein $R^{11}$ and $R^{12}$ are independently selected from H and halogen.

20. The compound according to claim 1, or a pharmaceutically acceptable salt thereof, wherein m and n are 1.

21. The compound according to claim 1, or a pharmaceutically acceptable salt thereof, wherein m, n, p, and q are 1.

22. The compound according to claim 1, wherein the compound is of formula (Ia):

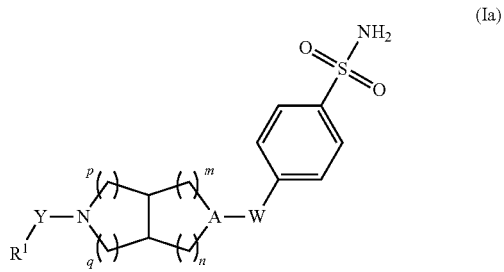

(Ia)

or a pharmaceutically acceptable salt thereof.

23. The compound according to claim 1, wherein the compound is:
- (3aR,6aS)-3,5-dichlorobenzyl 5-(4-(N-methylsulfamoyl)benzoyl)hexahydropyrrolo[3,4-c]pyrrole-2(1H)-carboxylate;
- (3aR,6aS)-3,5-dichlorobenzyl 5-(5-hydroxypicolinoyl)hexahydropyrrolo[3,4-c]pyrrole-2(1H)-carboxylate;
- (3aR,6aS)-3,5-dichlorobenzyl 5-(4-hydroxybenzoyl)hexahydropyrrolo[3,4-c]pyrrole-2(1H)-carboxylate;
- trans-3,5-dichlorobenzyl 2-(4-sulfamoylbenzoyl)hexahydro-1H-pyrrolo[3,4-c]pyridine-5(6H)-carboxylate;
- (3aR,6aS)-3,5-dichlorobenzyl 5-(5-sulfamoylthiophene-2-carbonyl)hexahydropyrrolo[3,4-c]pyrrole-2(1H)-carboxylate;
- (3aR,6aS)-3,5-dichlorobenzyl 5-(4-sulfamoylbenzoyl)hexahydropyrrolo[3,4-c]pyrrole-2(1H)-carboxylate;
- (3aR,6aS)-3,5-dichlorobenzyl 5-(4-aminobenzoyl)hexahydropyrrolo[3,4-c]pyrrole-2(1H)-carboxylate;
- (3aR,6aS)-3,5-dichlorobenzyl 5-(5-aminopicolinoyl)hexahydropyrrolo[3,4-c]pyrrole-2(1H)-carboxylate;
- (3aR,6aS)-3,5-dichlorobenzyl 5-(4-cyanobenzoyl)hexahydropyrrolo[3,4-c]pyrrole-2(1H)-carboxylate;
- (3aR,6aS)-3,5-dichlorobenzyl 5-(4-(methoxycarbonyl)benzoyl)hexahydropyrrolo[3,4-c]pyrrole-2(1H)-carboxylate;
- 4-{(3aS,8aR)-6-[(E)-3-(4-trifluoromethoxy-phenyl)-acryloyl]-octahydro-pyrrolo[3,4-d]azepine-2-carbonyl}-benzenesulfonamide;
- (3aS,6aS)-5-(3-fluoro-4-sulfamoyl-benzoyl)-hexahydro-pyrrolo[3,4-c]pyrrole-2-carboxylic acid 4-trifluoromethoxy-benzyl ester;
- (3aS,6aS)-5-(6-oxo-1,6-dihydro-pyridine-3-carbonyl)-hexahydro-pyrrolo[3,4-c]pyrrole-2-carboxylic acid 4-trifluoromethoxy-benzyl ester;
- (3aS,6aS)-5-(5-sulfamoyl-pyridine-2-carbonyl)-hexahydro-pyrrolo[3,4-c]pyrrole-2-carboxylic acid 4-trifluoromethoxy-benzyl ester;
- (3aS,6aS)-5-(1-methyl-4-sulfamoyl-1H-pyrrole-2-carbonyl)-hexahydro-pyrrolo[3,4-c]pyrrole-2-carboxylic acid 4-trifluoromethoxy-benzyl ester;
- (3aS,6aS)-5-(1-methyl-5-sulfamoyl-1H-pyrrole-2-carbonyl)-hexahydro-pyrrolo[3,4-c]pyrrole-2-carboxylic acid 4-trifluoromethoxy-benzyl ester;
- (3aS,6aS)-5-(6-sulfamoyl-pyridine-3-carbonyl)-hexahydro-pyrrolo[3,4-c]pyrrole-2-carboxylic acid 4-trifluoromethoxy-benzyl ester;
- (3aS,6aS)-5-(5-hydroxy-pyridine-2-carbonyl)-hexahydro-pyrrolo[3,4-c]pyrrole-2-carboxylic acid 4-trifluoromethoxy-benzyl ester;
- (3aS,6aS)-5-(4-hydroxy-benzoyl)-hexahydro-pyrrolo[3,4-c]pyrrole-2-carboxylic acid 4-trifluoromethoxy-benzyl ester;
- (3aR,6aS)-3,5-dichlorobenzyl 5-(4-acetamidobenzoyl)hexahydropyrrolo[3,4-c]pyrrole-2(1H)-carboxylate;
- (3aR,6aS)-3,5-dichlorobenzyl 5-(5-acetamidopicolinoyl)hexahydropyrrolo[3,4-c]pyrrole-2(1H)-carboxylate;
- (3aR,6aS)-3,5-dichlorobenzyl 5-(4-sulfamoylphenylsulfonyl)hexahydropyrrolo[3,4-c]pyrrole-2(1H)-carboxylate;
- (3aR,6aS)-3,5-dichlorobenzyl 5-(4-(1H-tetrazol-5-yl)benzoyl)hexahydropyrrolo[3,4-c]pyrrole-2(1H)-carboxylate;
- 4-((3aR,6aS)-5-((3,5-dichlorobenzyloxy)carbonyl)octahydropyrrolo[3,4-c]pyrrole-2-carbonyl)benzoic acid;
- (3aR,6aS)-3,5-dichlorobenzyl 5-(5-(methylsulfonamido)picolinoyl)hexahydropyrrolo[3,4-c]pyrrole-2(1H)-carboxylate;
- (3aS,6aS)-5-(4-sulfamoyl-benzoyl)-hexahydro-pyrrolo[3,4-c]pyrrole-2-carboxylic acid 3-chloro-5-methanesulfonyl-benzyl ester;
- (3aR,6aS)-5-(4-sulfamoyl-benzoyl)-hexahydro-pyrrolo[3,4-c]pyrrole-2-carboxylic acid 2-fluoro-4-trifluoromethoxy-benzyl ester;
- (3aR,6aS)-5-(4-sulfamoyl-benzoyl)-hexahydro-pyrrolo[3,4-c]pyrrole-2-carboxylic acid 4-trifluoromethoxy-benzyl ester;
- (3aS,6aS)-5-(4-sulfamoyl-benzoyl)-hexahydro-pyrrolo[3,4-c]pyrrole-2-carboxylic acid 4-trifluoromethoxy-benzyl ester;
- 4-{(3aR,6aR)-5-[3-(4-trifluoromethoxy-phenyl)-propionyl]-hexahydro-pyrrolo[3,4-c]pyrrole-2-carbonyl}-benzenesulfonamide;
- 4-{(3aR,6aR)-5-[(E)-3-(4-trifluoromethoxy-phenyl)-acryloyl]-hexahydro-pyrrolo[3,4-c]pyrrole-2-carbonyl}-benzenesulfonamide;
- 4-[(3aR,6aS)-5-(4-isopropoxy-naphthalene-2-carbonyl)-hexahydro-pyrrolo[3,4-c]pyrrole-2-carbonyl]-benzenesulfonamide;
- 4-{(3aR,6aS)-5-[1-(2,2,2-trifluoro-ethoxy)-isoquinoline-3-carbonyl]-hexahydro-pyrrolo[3,4-c]pyrrole-2-carbonyl}-benzenesulfonamide;
- 4-[(3aR,6aS)-5-(1-Methyl-5-trifluoromethoxy-1H-indole-2-carbonyl)-hexahydro-pyrrolo[3,4-c]pyrrole-2-carbonyl]-benzenesulfonamide;
- 4-[(3aR,6aS)-5-(4-Isopropoxy-quinoline-2-carbonyl)-hexahydro-pyrrolo[3,4-c]pyrrole-2-carbonyl]-benzenesulfonamide;
- 4-[(3aS,6aR)-5-(4'-chloro-biphenyl-4-carbonyl)-hexahydro-pyrrolo[3,4-c]pyrrole-2-carbonyl]-benzenesulfonamide;
- 4-{(3aS,6aR)-5-[3-(2-fluoro-4-trifluoromethoxy-phenyl)-propionyl]-hexahydro-pyrrolo[3,4-c]pyrrole-2-carbonyl}-benzenesulfonamide;
- 4-{(3aS,6aR)-5-[3-(4-trifluoromethoxy-phenyl)-propionyl]-hexahydro-pyrrolo[3,4-c]pyrrole-2-carbonyl}-benzenesulfonamide;

4-((3aR,6aR)-5-(3-(2-fluoro-4-(trifluoromethoxy)phenyl)
propanoyl)octahydropyrrolo[3,4-c]pyrrole-2-carbonyl)
benzenesulfonamide;
(+)-trans-3,5-dichlorobenzyl 2-(4-sulfamoylbenzoyl)
hexahydro-1H-pyrrolo[3,4-c]pyridine-5(6H)-carboxylate;
(−)-trans-3,5-dichlorobenzyl 2-(4-sulfamoylbenzoyl)
hexahydro-1H-pyrrolo[3,4-c]pyridine-5(6H)-carboxylate;
(3aS,6aS)-5-(2-fluoro-4-sulfamoyl-benzoyl)-hexahydropyrrolo[3,4-c]pyrrole-2-carboxylic acid 4-trifluoromethoxy-benzyl ester;
5-{(3aR,6aR)-5-[3-(4-trifluoromethoxy-phenyl)-propionyl]-hexahydro-pyrrolo[3,4-c]pyrrole-2-carbonyl}-pyridine-2-sulfonic acid amide;
5-((3aS,6aS)-5-(4-ethoxyquinoline-2-carbonyl)octahydropyrrolo[3,4-c]pyrrole-2-carbonyl)pyridine-2-sulfonamide;
(3aS,6aS)-5-(3-fluoro-4-sulfamoyl-benzoyl)-hexahydropyrrolo[3,4-c]pyrrole-2-carboxylic acid 4-cyano-2-(2,2-dimethyl-propionylamino)-benzyl ester;
(3aS,6aS)-5-(6-sulfamoyl-pyridine-3-carbonyl)-hexahydro-pyrrolo[3,4-c]pyrrole-2-carboxylic acid 4-cyano-2-(2,2-dimethyl-propionylamino)-benzyl ester;
(3aS,6aS)-5-(4-sulfamoyl-benzoyl)-hexahydro-pyrrolo[3,4-c]pyrrole-2-carboxylic acid 4-cyano-2-(2,2-dimethyl-propionylamino)-benzylester;
(3aS,6aS)-5-(2-fluoro-4-sulfamoyl-benzoyl)-hexahydro-pyrrolo[3,4-c]pyrrole-2-carboxylic acid 4-cyano-2-(2,2-dimethyl-propionylamino)-benzyl ester; or
(3aS,6aS)-5-(5-sulfamoyl-pyridine-2-carbonyl)-hexahydro-pyrrolo[3,4-c]pyrrole-2-carboxylic acid 4-cyano-2-(2,2-dimethyl-propionylamino)-benzyl ester;
or a pharmaceutically acceptable salt thereof.

24. The compound according to claim 1, wherein the compound is:
(3aR,6aS)-3,5-dichlorobenzyl 5-(4-sulfamoylbenzoyl)hexahydropyrrolo[3,4-c]pyrrole-2(1H)-carboxylate;
(3aS,6aS)-5-(3-fluoro-4-sulfamoyl-benzoyl)-hexahydropyrrolo[3,4-c]pyrrole-2-carboxylic acid 4-trifluoromethoxy-benzyl ester;
(3aS,6aS)-5-(5-sulfamoyl-pyridine-2-carbonyl)-hexahydro-pyrrolo[3,4-c]pyrrole-2-carboxylic acid 4-trifluoromethoxy-benzyl ester;
(3aS,6aS)-5-(6-sulfamoyl-pyridine-3-carbonyl)-hexahydro-pyrrolo[3,4-c]pyrrole-2-carboxylic acid 4-trifluoromethoxy-benzyl ester;
(3aS,6aS)-5-(4-sulfamoyl-benzoyl)-hexahydro-pyrrolo[3,4-c]pyrrole-2-carboxylic acid 4-trifluoromethoxy-benzyl ester;
4-{(3aR,6aR)-5-[3-(4-trifluoromethoxy-phenyl)-propionyl]-hexahydro-pyrrolo[3,4-c]pyrrole-2-carbonyl}-benzenesulfonamide; or
(3aS,6aS)-5-(5-sulfamoyl-pyridine-2-carbonyl)-hexahydro-pyrrolo[3,4-c]pyrrole-2-carboxylic acid 4-cyano-2-(2,2-dimethyl-propionylamino)-benzyl ester;
or a pharmaceutically acceptable salt thereof.

25. A process to prepare a compound according to claim 1, comprising reacting a compound of formula (II) in the presence of a compound of formula (III), wherein $R^1$, $R^2$, A, W, m, n, p and q are as defined for formula (I), and Y is —OC(O)—:

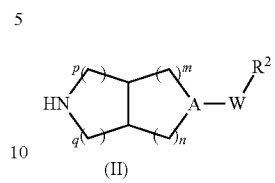
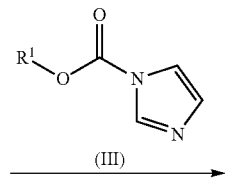
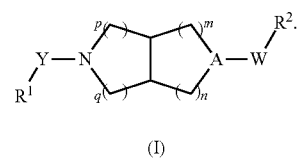

26. A pharmaceutical composition comprising a compound according to claim 1, or a pharmaceutically acceptable salt thereof, and a therapeutically inert carrier.

27. A method for the treatment of a condition, wherein the condition is an ocular condition, comprising administering an effective amount of a compound according to claim 1, or a pharmaceutically acceptable salt thereof.

28. The compound of claim 1, or a pharmaceutically acceptable salt thereof, manufactured by:
reacting a compound of formula (II) in the presence of a compound of formula (III), wherein $R^1$, $R^2$, A, W, m, n, p and q are as defined for formula (I), and Y is —OC(O)—:

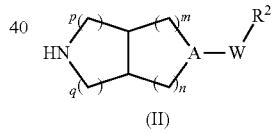
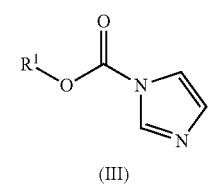
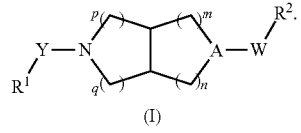

29. A pharmaceutical composition comprising a compound according to claim 23, or a pharmaceutically acceptable salt thereof, and a therapeutically inert carrier.

30. The compound according to claim 1, wherein the compound is (3aS,6aS)-5-(2-fluoro-4-sulfamoyl-benzoyl)-hexahydro-pyrrolo[3,4-c]pyrrole-2-carboxylic acid 4-trifluoromethoxy-benzyl ester, or a pharmaceutically acceptable salt thereof.

31. A pharmaceutical composition comprising a compound according to claim 24, or a pharmaceutically acceptable salt thereof, and a therapeutically inert carrier.

32. A pharmaceutical composition comprising a compound according to claim 30, or a pharmaceutically acceptable salt thereof, and a therapeutically inert carrier.

33. The method of claim 27, wherein the ocular condition is proliferative retinopathy, non-proliferative retinopathy, dry age-related macular degeneration, wet age-related macular degeneration, macular edema, central arterial occlusion, central venous occlusion, traumatic injury, or glaucoma.

34. A method for the treatment of a condition, wherein the condition is an ocular condition, comprising administering an effective amount of a compound according to claim 23, or a pharmaceutically acceptable salt thereof.

35. The method of claim 34, wherein the ocular condition is proliferative retinopathy, non-proliferative retinopathy, dry age-related macular degeneration, wet age-related macular degeneration, macular edema, central arterial occlusion, central venous occlusion, traumatic injury, or glaucoma.

36. A method for the treatment of a condition, wherein the condition is an ocular condition, comprising administering an effective amount of a compound according to claim 24, or a pharmaceutically acceptable salt thereof.

37. The method of claim 36, wherein the ocular condition is proliferative retinopathy, non-proliferative retinopathy, dry age-related macular degeneration, wet age-related macular degeneration, macular edema, central arterial occlusion, central venous occlusion, traumatic injury, or glaucoma.

38. A method for the treatment of a condition, wherein the condition is an ocular condition, comprising administering an effective amount of a compound according to claim 30, or a pharmaceutically acceptable salt thereof.

39. The method of claim 38, wherein the ocular condition is proliferative retinopathy, non-proliferative retinopathy, dry age-related macular degeneration, wet age-related macular degeneration, macular edema, central arterial occlusion, central venous occlusion, traumatic injury, or glaucoma.

* * * * *